(12) United States Patent
Teitelbaum et al.

(10) Patent No.: US 8,293,776 B2
(45) Date of Patent: Oct. 23, 2012

(54) COMPOSITIONS AND METHODS FOR TREATING INFLAMMATORY CONDITIONS OF THE BOWEL

(75) Inventors: Daniel H. Teitelbaum, Ann Arbor, MI (US); Hollis Showalter, Ann Arbor, MI (US); Scott Larsen, South Lyon, MI (US); Peter Lucas, Ann Arbor, MI (US); Hiroyuki Koga, Tokyo (JP)

(73) Assignee: The Regents of the University of Michigan, Ann Arbor, MI (US)

( * ) Notice: Subject to any disclaimer, the term of this patent is extended or adjusted under 35 U.S.C. 154(b) by 108 days.

(21) Appl. No.: 12/536,390

(22) Filed: Aug. 5, 2009

(65) Prior Publication Data
US 2010/0035852 A1 Feb. 11, 2010

Related U.S. Application Data

(60) Provisional application No. 61/086,393, filed on Aug. 5, 2008, provisional application No. 61/177,054, filed on May 11, 2009.

(51) Int. Cl.
*A61K 31/41* (2006.01)
(52) U.S. Cl. ......... 514/381; 514/382; 514/383; 514/384
(58) Field of Classification Search ........... 514/381–384
See application file for complete search history.

(56) References Cited

U.S. PATENT DOCUMENTS

| | | | |
|---|---|---|---|
| 5,128,355 A * | 7/1992 | Carini et al. | 514/381 |
| 5,212,195 A * | 5/1993 | Clark et al. | 514/381 |
| 5,223,409 A | 6/1993 | Ladner | |
| 2005/0209141 A1 * | 9/2005 | Silver et al. | 514/12 |
| 2005/0282877 A1 * | 12/2005 | Becker et al. | 514/381 |
| 2006/0154975 A1 | 7/2006 | Yang et al. | |
| 2006/0211752 A1 | 9/2006 | Kohn et al. | |
| 2007/0123499 A1 | 5/2007 | Teitelbaum et al. | |

OTHER PUBLICATIONS

Campieri, Gut, 2002;50:43-46.*
Remington Pharmaceutical Science, vol. II,19th ed., 1995, p. 1403.*
Beckman et al., Apparent hydroxyl radical production by peroxynitrite: implications for endothelial injury from nitric oxide and superoxide, Proc. Natl. Acad. Sci. U.S.A. 1990, 87, 1620-1624.
Benigni et al., Endothelin antagonists and renal protection, J Cardiovasc Pharmacol. 2000, 35(4 Suppl 2): S75-78.
Brooks, Effect of captopril and the nonpeptide angiotensin II antagonists, SK&F 108566 and EXP3174, on renal function in dogs with a renal artery stenosis., J Pharmacol Exp Ther. Nov. 1992;263(2):422-7.
Houghten, The use of synthetic peptide combinatorial libraries for the identification of bioactive peptides, Biotechniques 13:412-421 (1992).

(Continued)

*Primary Examiner* — San-Ming Hui
(74) *Attorney, Agent, or Firm* — Casimir Jones, S.C.

(57) ABSTRACT

The present invention provides compositions and methods for treating inflammatory conditions (e.g., of the bowel). In particular, the present invention provides methods of treating (e.g., therapeutically and/or prophylactically treating) inflammatory conditions (e.g., of the bowel), compositions useful for such methods (e.g., antagonists and/or inhibitors of angiotensin II (AngII) receptor Type 1a (AT1a)), and methods of identifying, characterizing and/or optimizing such compositions. Compositions and methods of the present invention find use in, among other things, clinical (e.g. therapeutic and preventative medicine) and research applications.

10 Claims, 24 Drawing Sheets

OTHER PUBLICATIONS

Carell et al., A Novel Procedure for the Synthesis of Libraries Containing Small Organic Molecules, Angew. Chem. Int. Ed. Engl., vol. 33, Issue 20, 33:2061 (1994).
Cho et al., An unnatural biopolymer, Science 261:1303 (1993).
Cull et al., Screening for receptor ligands using large libraries of peptides linked to the C terminus of the lac repressor, Proc. Nat. Acad. Sci. USA 89:1865-1869 (1992).
Cwirla et al., Peptides on phage: a vast library of peptides for identifying ligands, Proc. Natl. Acad. Sci. 87:6378-6382 (1990).
Davéet al., Amelioration of chronic murine colitis by peptide-mediated transduction of the IkappaB kinase inhibitor NEMO binding domain peptide, J Immunol. Dec. 1, 2007;179(11):7852-9.
Devlin, Random peptide libraries: a source of specific protein binding molecules, Science 249:404-406 (1990).
DeWitt et al., "Diversomers": an approach to nonpeptide, nonoligomeric chemical diversity, Proc. Natl. Acad. Sci. U.S.A. 90:6909 (1993).
Duncia et al., The discovery of DuP 753, a potent, orally active nonpeptide angiotensin II receptor antagonist, Med. Res. Rev. Mar. 1992;12(2):149-91.
Duncia et al., The discovery of potent nonpeptide angiotensin II receptor antagonists: a new class of potent antihypertensives, J Med Chem 1990 33: 1312-1329.
Erb et al., Recursive deconvolution of combinatorial chemical libraries, Proc. Nad. Acad. Sci. USA 91:11422 (1994).
Felici, Selection of antibody ligands from a large library of oligopeptides expressed on a multivalent exposition vector, J. Mol. Biol. 222:301 (1991).
Fodor, Multiplexed biochemical assays with biological chips, Nature 364:555-556 (1993).
Gallop et al., Applications of combinatorial technologies to drug discovery. 1. Background and peptide combinatorial libraries, J. Med. Chem. 37:1233 (1994).
Hayden et al., NF-kappaB and the immune response, Oncogene. Oct. 30, 2006;25(51):6758-80.
Israili, Clinical pharmacokinetics of angiotensin II (AT1) receptor blockers in hypertension, J. Hum. Hypertens. 2000, 14 (Suppl. 1), S73-S86.
Carini, Nonpeptide angiotensin II receptor antagonists: the discovery of a series of N-(biphenylylmethyl)imidazoles as potent, orally active antihypertensives, J Med Chem. Aug. 1991;34(8):2525-47.
Kagami et al., Angiotensin II stimulates extracellular matrix protein synthesis through induction of transforming growth factor-beta expression in rat glomerular mesangial cells, J. Clin. Invest. 1994, 93, 2431-2437.
Lam, Application of combinatorial library methods in cancer research and drug discovery, Anticancer Drug Des. Apr. 1997;12(3):145-167.
Lam, A new type of synthetic peptide library for identifying ligand-binding activity, Nature. Nov. 7, 1991;354(6348):82-4.
Mayer, Pharmacological targeting of signaling pathways in protein kinase C-stimulated superoxide generation in neutrophil-like HL-60 cells: effect of phorbol ester, arachidonic acid and inhibitors of kinase(s), phosphatase(s) and phospholipase A2, J Pharmacol Exp Ther. Nov. 1996;279(2):633-44.
McAllister-Lucas et al., CARMA3/Bcl10/MALT1-dependent NF-kappaB activation mediates angiotensin II-responsive inflammatory signaling in nonimmune cells, Proc Natl Acad Sci U S A. Jan. 2, 2007; 104(1):139-44. Epub Nov. 13, 2006.
Nenci et al., Epithelial NEMO links innate immunity to chronic intestinal inflammation, Nature. Mar. 29, 2007;446 (7135):557-61. Epub Mar. 14, 2007.
Phillips et al., Angiotensin II as a pro-inflammatory mediator, Curr Opin Investig Drugs. Apr. 2002;3(4):569-77.
Pollman et al., Vasoactive substances regulate vascular smooth muscle cell apoptosis. Countervailing influences of nitric oxide and angiotensin II, Circ Res. Oct. 1996;79(4):748-56.
Protective Groups in Organic Chemistry, ed. J.F.W. McOmie, Plenum Press, 1973 (book—no copy is provided at this time).
Raij et al., Glomerular actions of nitric oxide, Kidney Int. Jul. 1995;48(1):20-32.
Scott and Smith, Searching for peptide ligands with an epitope library, Science. Jul. 27, 1990;249(4967):386-90.
Spencer et al., Reduced severity of a mouse colitis model with angiotensin converting enzyme inhibition, Dig Dis Sci. Apr. 2007;52(4):1060-70. Epub Mar. 7, 2007.
T.W. Greene & P.G.M. Wuts, Protective Groups in Organic Synthesis, John Wiley & Sons, 1991 (book—no copy is provided at this time).
Unger et al., Pharmacology of AT1-receptor blockers, Blood Press Suppl. 2001;(3):5-10.
Vauquelin et al., Insurmountable AT(1) receptor antagonism: the need for different antagonist binding states of the receptor, Trends Pharmacol Sci. Jul. 2001;22(7):343-4.
Veber et al., Molecular properties that influence the oral bioavailability of drug candidates, J Med Chem. Jun. 6, 2002;45(12):2615-23.
Wolny et al., Functional and biochemical analysis of angiotensin II-forming pathways in the human heart, Circ Res. Feb. 1997;80(2):219-27.
Wong et al., Nonpeptide angiotensin II receptor antagonists. VIII. Characterization of functional antagonism displayed by DuP 753, an orally active antihypertensive agent, J Pharmacol Exp Ther. Feb. 1990;252(2):719-25.
Zuckerann et al., Discovery of nanomolar ligands for 7-transmembrane G-protein-coupled receptors from a diverse N-(substituted)glycine peptoid library, J Med Chem. Aug. 19, 1994;37(17):2678-85.
Taylor, Divergent Effects of Angiotensin-Converting Enzyme Inhibition and Angiotensin II-Receptor Antagonism on Myocardial Cellular Proliferation and Collagen Deposition After Myocardial Infarction in Rats, Journal of Cardiovascular Pharmacology: May 1998—vol. 31—Issue 5—pp. 654-660.

* cited by examiner

A

B

C

D

E

F

A)

B

C

D

E

COMPOSITIONS AND METHODS FOR TREATING INFLAMMATORY CONDITIONS OF THE BOWEL

This Application claims priority to U.S. Provisional Patent Application Ser. Nos. 61/086,393 filed 5 Aug. 2008 and 61/177,054 filed 11 May 2009, each of which is hereby incorporated by reference in its entirety.

This invention was made with government support under AI44076-09 awarded by the National Institutes of Health. The government has certain rights in the invention.

FIELD OF THE INVENTION

The present invention provides compositions and methods for treating inflammatory conditions (e.g., of the bowel). In particular, the present invention provides methods of treating (e.g., therapeutically and/or prophylactically treating) inflammatory conditions (e.g., of the bowel), compositions useful for such methods (e.g., antagonists and/or inhibitors of angiotensin II (AngII) receptor Type 1a (AT1a)), and methods of identifying, characterizing and/or optimizing such compositions. Compositions and methods of the present invention find use in, among other things, clinical (e.g. therapeutic and preventative medicine) and research applications.

BACKGROUND OF THE INVENTION

Inflammatory Bowel Disease (IBD) refers to a group of gastrointestinal disorders characterized by a chronic non-specific inflammation of portions of the gastrointestinal tract. Ulcerative colitis and Crohn's Disease are the most prominent examples of IBD in humans. They are associated with many symptoms and complications, including growth retardation in children, rectal prolapse, blood in stools (e.g., melena and/or hematochezia), wasting, iron deficiency, and anemia (e.g. iron deficiency anemia and anemia of chronic disease or of chronic inflammation).

The etiology (or etiologies) and pathogenesis of IBD are still unclear. Previous understanding of the pathogenesis was limited to a three-stage process: (a) an irritant, which could be an immune process or infectious agent, activates (b) leukocytes which release enzymes such as pro-inflammatory cytokines (including tumor necrosis factor alpha (TNF-α), IL-1β and IL-6), proteases and inflammatory mediators such as histamine, serotonin and prostaglandins, and (c) these immunological agents causing edema, pain, heat and loss of function. During the inflammatory process one sees a decline in anti-inflammatory cytokines (including a decline in IL-10). (See, e.g., Wyngaarden and Smith (eds.) Cecil's Textbook of Medicine (W. B. Saunders Co. 1985), Berkow (ed.)), and Harrison's Principles of Internal Medicine, 12th Ed., McGraw-Hill, Inc. (1991)).

Numerous theories implicate multiple factors leading up to IBD including genetic predisposition, environmental factors, infectious agents and immunologic alterations (See e.g., Kirsner, J. B., et al. (eds), Inflammatory Bowel Disease, 3rd ed., Lea and Febiger, Philadelphia (1988); Zipser, R. D., (ed.), Dig. Dis. Sci., 33 Suppl.:1S-87S (1988)). The immunologic alterations in IBD appear to be autoimmune in nature, with autoantibodies and lymphocyte-cytotoxicity directed against intestinal epithelial cells. However, even the latest developments in the immunologic aspects of the pathogenesis of IBD cannot answer the basic question, i.e., whether the detected changes in humoral and cellular immunity reflect a primary defect or secondary response to injury.

Treatment for IBD currently includes steroids, sulphasalazine and its derivatives, and drugs such as cyclosporin A, mercaptopurine and azathioprine. Such therapies are directed toward suppression of the general immune response. These approaches often result in poor success, have little or no selectivity, and can be accompanied by unwanted and sometimes dangerous consequential side effects.

SUMMARY OF THE INVENTION

The present invention provides compositions and methods for treating inflammatory conditions (e.g., of the bowel). In particular, the present invention provides methods of treating (e.g., therapeutically and/or prophylactically treating) inflammatory conditions (e.g., of the bowel), compositions useful for such methods (e.g., antagonists and/or inhibitors of angiotensin II (AngII) receptor Type 1a (AT1a)), and methods of identifying, characterizing and/or optimizing such compositions. Compositions and methods of the present invention find use in, among other things, clinical (e.g. therapeutic and preventative medicine) and research applications.

Accordingly, in some embodiments, the present invention provides a method of treating a subject, comprising: providing: a subject with inflammatory bowel disease, and a composition comprising an angiotensin II (AngII) receptor Type 1a (AT1a) antagonist, or derivative thereof, that is poorly cell permeable (e.g., that is poorly absorbed via the gastrointestinal tract (e.g., that leads to very low to undetectable levels of AT1a antagonist in the circulatory system of a subject administered the antagonist)) and; administering the composition to the subject under conditions such that the severity of inflammatory bowel disease is reduced in the subject. In some embodiments, the composition comprising an AT1a antagonist or derivative thereof is suspended in polyethylene glycol (e.g., of 1000 molecular weight). In some embodiments, the composition comprising an AT1a antagonist or derivative thereof is suspended in a neutral buffer (e.g., water or other pharmaceutically acceptable buffer described herein). In some embodiments, the composition comprising an AT1a antagonist or derivative thereof is co-administered with another agent (e.g., a corticosteroid, angiotensis converting enzyme (ACE) inhibitor (ACE-I), or other type of anti-inflammatory agent (e.g., anti-TNF-α, etc.) etc. In some embodiments, the AT1a antagonist or derivative thereof is administered to the subject in a dose of about 0.5 g/kg to 1 mg/kg, although higher (e.g., 1-2, 2-4, 4-10, 10-20, 20-50, 50-100, 100-500, 500-1000 mg/kg, or higher) and lower (e.g., 0.25-0.5, 0.125-0.25, 0.01-0.125, 0.001-0.01 mg/kg) doses also find use in the invention. In a preferred embodiment, a composition comprising an AT1a antagonist or derivative thereof is enterally administered. In some embodiments, a composition comprising an AT1a antagonist or derivative thereof is orally administered. In some embodiments, a composition comprising an AT1a antagonist or derivative thereof is administered rectally. In some embodiments, administering rectally comprises an enema. The present invention is not limited by the route of administration. Indeed, a composition of the present invention can be administered via any route described herein. Similarly, the present invention is not limited by the type of subject that benefits from administration of a composition of the present invention. In some embodiments, the subject has an inflammatory disease. In some embodiments, the inflammatory disease is inflammatory bowel disease. In some embodiments, the inflammatory bowel disease is Crohn's disease, irritable bowel syndrome, celiac disease, ulcerative colitis, stomach ulcers, diverticulitis, pouchitis, proctitis and/or chronic diarrhea. In some embodiments, the AT1a antagonist or derivative thereof is a derivative of losartan or a derivative of candesartan. However, the present invention is not so limited. For example, in some embodiments, a compositions of the present invention comprise a derivative and/or analog of any sartan family member including, but not limited to, azilsartan, eprosartan, irbesartan, valsartan, olmesartan, telmisartan and tasosartan. In some embodiments, a compositions of the present invention comprise a derivative and/or analog of a sartan family member that has been modified to decrease the sartan family member's cellular permeability (e.g., thereby decreasing its absorbance via the gastrointestinal tract (e.g., thereby leading to low to undetectable levels of sartan in the circulatory system of a subject administered the sartan)). In some embodiments, a reduction in the severity of inflammatory bowel disease in the subject is detectable by a decrease in the clinical severity of colitis in the subject. In some embodiments, the reduction of the severity of inflammatory bowel disease in the subject is detectable by a reduction in histologic score in the subject.

The present invention also provides a method of treating a subject comprising: providing: a subject at risk for inflammatory bowel disease, and a composition comprising an AT1a antagonist or derivative thereof, and; administering the composition to the subject so as to prevent the subject from experiencing symptoms of inflammatory bowel disease. In some embodiments, the administration of the composition delays the onset of symptoms of inflammatory bowel disease (e.g., including, but not limited to, heme positive stools and the loss of body weight). In some embodiments, the composition comprising an AT1a antagonist or derivative thereof is co-administered with another agent (e.g., a corticosteroid, ACE-I, or other type of anti-inflammatory agent (e.g., anti-TNF-α, etc.) etc. In some embodiments, the composition comprising an AT1a antagonist or derivative thereof is administered via an enteric route (e.g., orally and/or rectally).

The present invention also provides a composition comprising an AT1a antagonist or derivative thereof and another agent (e.g., anti-inflammatory agent (e.g., corticosteroid, anti-TNF-α), an angiotensin converting enzyme inhibitor, or other agent). In some embodiments, the composition comprises one or more other agents. The present invention is not limited by the type of agent. For example, the agent may be an ACE inhibitor, polyethylene glycol, a steroid (e.g., prednisone or cortisol) or other agent that finds use in a composition of the present invention described herein (e.g., for the treatment of inflammatory disease (e.g., inflammatory bowel disease)). In some embodiments, the angiotensin converting enzyme inhibitor is suspended in polyethylene glycol (PEG). The present invention is not limited by the type of PEG. In some embodiments, a composition of the invention comprises PEG with a molecular weight of 200, 300, 400, 600, 1000, 1450, 3350, 4000, 6000, 8000 or 20000. In some embodiments, a composition comprises a 1000-1500 molecular weight PEG. In some embodiments, a composition comprising an AT1a antagonist or derivative thereof comprises a 1000-1450 molecular weight PEG. The present invention is not limited by the type of ACE inhibitor co-administered with a composition comprising and AT1a antagonist or derivative thereof. Indeed, a variety of ACE inhibitors find use in the invention including, but not limited to, alacepril, benazepril, captopril, cilazapril, ceranapril, delapril, enalapril, enalaprilat, fosinopril, fosinoprilat, imidapril, lisinopril, moexipril, perindopril, perindoprilat, quinapril, quinaprilat, ramipril, saralasin acetate, spirapril, temocapril, trandolapril, fasidotrilat, beclometasone dipropionate, FPL-66564, idrapril, MDL-100240, and S-5590.

In some preferred embodiments, compositions of the present invention are administered enterally (e.g., rectally (e.g., as an enema) or orally). The present invention is not limited to any particular route of administration. Indeed, a variety of administrative routes are contemplated to be useful for delivery of a compositions of the present invention including, but not limited to, orally, parenterally, topically, and intravenously.

Compositions and method of the present invention find use in the therapeutic and/or prophylactic treatment of a variety of inflammatory bowel diseases. In some embodiments, the subject possesses symptoms of inflammatory bowel disease. In some embodiments, the subject is suffering from Crohn's disease. In other embodiments, the subject is suffering from ulcerative colitis. In still further embodiments, the subject is suffering from irritable bowel syndrome, celiac disease, stomach ulcers, diverticulitis, pouchitis, proctitis, mucositis, radiation-associated enteritis, short bowel disease, or chronic diarrhea. In some embodiments, administration of a composition comprising AT1a antagonist or derivative thereof to a subject reduces the signs and/or symptoms of disease (e.g. reduces the symptoms of inflammatory bowel disease, Crohn's disease, ulcerative colitis, irritable bowel syndrome, celiac disease, stomach ulcers, diverticulitis, pouchitis, proctitis, or chronic diarrhea) in the subject. In some embodiments, a composition comprising an AT1a antagonist or derivative thereof is administered to a subject under conditions such that symptoms of inflammatory bowel disease are reduced in the subject. In other embodiments, a subject at risk for inflammatory bowel disease is prophylactically administered a therapeutic composition comprising an AT1a antagonist or derivative thereof. In further embodiments, a therapeutically effective amount of a composition comprising an AT1a antagonist or derivative thereof is administered to the subject. In some embodiments, a composition comprising an AT1a antagonist or derivative thereof is administered in conjunction with one or more other therapeutic compounds (e.g., known therapeutic compounds such as steroids or ACE inhibitors). In some embodiments, when co-administered with a composition comprising an AT1a antagonist or derivative thereof, a therapeutic agent (e.g., a steroid or ACE inhibitor) is administered to a subject at a lower dose than if given without a composition comprising an AT1a antagonist or derivative thereof (e.g., while providing the same or better therapeutic benefit to a subject receiving a higher dose of the therapeutic agent (e.g., a steroid or ACE inhibitor) in the absence of co-administration of a composition comprising an AT1a antagonist or derivative thereof). In some preferred embodiments, a composition comprising an AT1a antagonist or derivative thereof is co-administered with a corticosteroid. In some embodiments, the corticosteroid is prednisone. In other preferred embodiments, a composition comprising an AT1a antagonist or derivative thereof is co-administered with an ACE inhibitor. It is not intended that the present invention be limited to a particular ACE inhibitor. Indeed, a variety of ACE inhibitors are contemplated including, but not limited to, alacepril, benazepril, captopril, cilazapril, ceranapril, delapril, enalapril, enalaprilat, fosinopril, fosinoprilat, imidapril, lisinopril, moexipril, perindopril, perindoprilat, quinapril, quinaprilat, ramipril, saralasin acetate, spirapril, temocapril, trandolapril, fasidotrilat, beclometasone dipropionate, FPL-66564, idrapril, MDL-100240, and S-5590.

The present invention also provides a method of treatment, comprising, providing a subject at risk for inflammatory bowel disease and a composition comprising an AT1a antagonist or derivative thereof, and administering to the subject a therapeutically effective amount of the composition so as to prevent the subject from experiencing signs or symptoms of inflammatory bowel disease, related inflammatory conditions of the gastrointestinal tracts, or other gastrointestinal disorders. In some embodiments, the administration of the therapeutic composition comprising an AT1a antagonist or derivative thereof delays the progression of the signs or symptoms of inflammatory bowel disease. In one embodiment, the subject at risk for inflammatory bowel disease is a human. In a preferred embodiment, the human is selected from a young adult, a person living in the United States, a person living in England, a person living in Northern Europe, a person of Jewish descent, a person living in a developing nation, a person with family members who suffer from inflammatory bowel disease or a person determined to carry an inflammatory bowel disease risk gene. In a particularly preferred embodiment, the administration to a subject of a therapeutic composition comprising an AT1a antagonist or derivative thereof prevents the onset of one or more signs or symptoms of inflammatory bowel disease (e.g. prevents the onset of abdominal pain, diarrhea, rectal bleeding, weight loss, fever, loss of appetite, dehydration, anemia, or malnutrition, or any combination thereof) in the subject.

In some embodiments, a composition comprising an AT1a antagonist or derivative thereof is administered orally to a subject at risk for inflammatory bowel disease. In other embodiments, a composition is administered to the subject parenterally, topically, or intravenously. In still further embodiments, the composition comprises a transdermal patch. In some embodiments, a composition comprising an AT1a antagonist or derivative thereof is administered rectally (e.g., via an enema). In some embodiments, administration of a composition described herein prevents intestinal fibrosis (e.g., resulting from inflammatory bowel disease (e.g., Crohn's disease)).

In some embodiments, a subject at risk for developing gastrointestinal inflammation or inflammatory bowel disease is at risk for developing Crohn's disease, irritable bowel syndrome, celiac disease, ulcerative colitis, stomach ulcers, diverticulitis, pouchitis, proctitis, mucositis, radiation-induced enteritis or chronic diarrhea. However, the present invention is not so limited. For example, a composition comprising an AT1a antagonist or derivative thereof may be administered to any subject at risk for showing signs or symptoms of inflammation. For example, in some embodiments, compositions of the present invention may be administered to a subject in any defined, localized area (e.g., including, but not limited to, the lungs (e.g., via inhalational therapy), a joint space (e.g., via injection), the biliary tract, etc.) for treating and/or preventing signs or symptoms of inflammatory conditions and/or inflammatory diseases.

DESCRIPTION OF THE DRAWINGS

FIG. 3 shows losartan 1 and the losartan variant 1a.

FIG. 8 shows that the losartan analog compound 2 significantly inhibits ANG II signaling via AT1a.

DEFINITIONS

Figure 1:
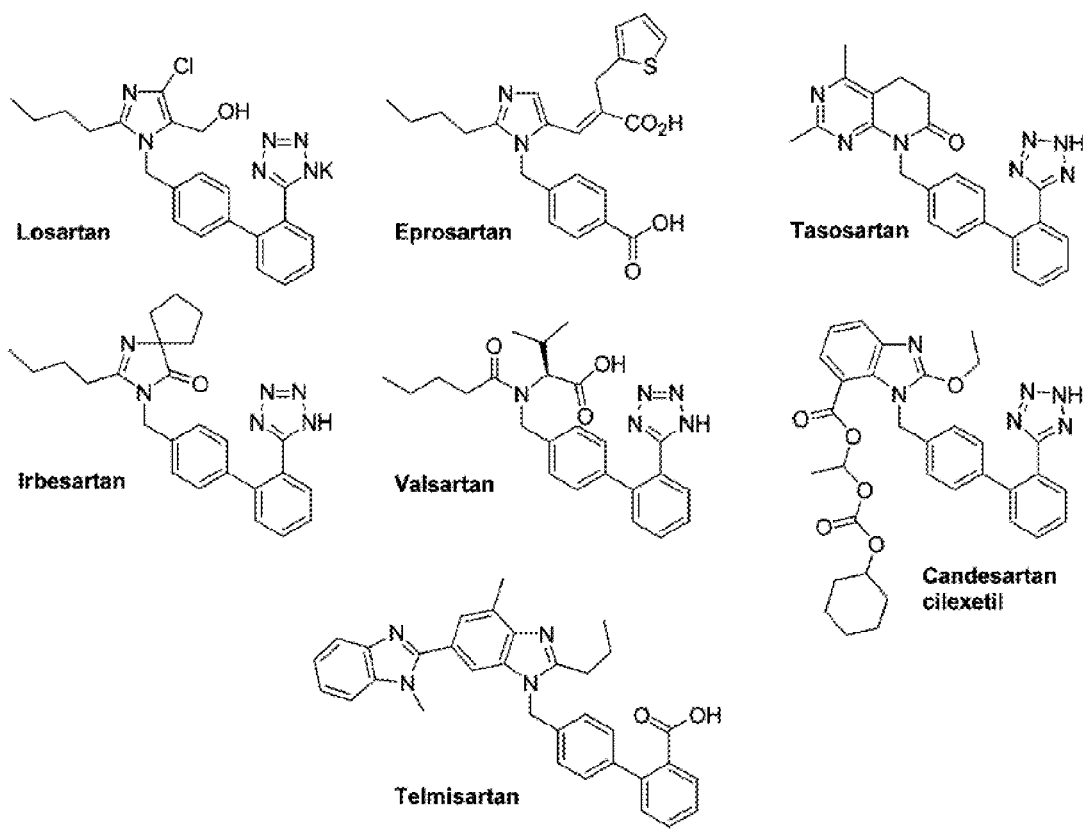
FIG. 1 shows members of the sartane family.

To facilitate an understanding of the present invention, a number of terms and phrases are defined below:

"Gastrointestinal inflammation" as used herein refers to inflammation of a mucosal layer of the gastrointestinal tract (e.g., encompassing acute and chronic inflammatory conditions). Acute inflammation is generally characterized by a short time of onset and infiltration or influx of neutrophils. Chronic inflammation is generally characterized by a relatively longer period of onset and infiltration or influx of mononuclear cells. Chronic inflammation is also typically characterized by periods of spontaneous remission and spontaneous occurrence. "Mucosal layer of the gastrointestinal tract" is meant to include mucosa of the bowel (e.g., including the small intestine and large intestine), rectum, stomach (gastric) lining, oral cavity, and the like.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is associated with infiltration or influx of mononuclear cells and can be further associated with periods of spontaneous remission and spontaneous occurrence. Thus, subjects with "chronic gastrointestinal inflammation" may be expected to require a long period of supervision, observation, and/or care. "Chronic gastrointestinal inflammatory conditions" (also referred to as "chronic gastrointestinal inflammatory diseases") having such chronic inflammation include, but are not necessarily limited to, inflammatory bowel disease (IBD), colitis (e.g., induced by environmental insults (e.g., gastrointestinal inflammation (e.g., colitis) caused by or associated with (e.g., as a side effect of) a therapeutic regimen (e.g., administration of chemotherapy, radiation therapy, and the like))), and/or associated with chronic granulomatous disease (See, e.g., Schappi et al., Arch. Dis. Child., 1984:147 (2001)), celiac disease, celiac sprue (a heritable disease in which the intestinal lining is inflamed in response to the ingestion of a protein known as gluten), food allergies, gastritis, infectious gastritis and/or enterocolitis (e.g., *Helicobacter pylori*-infected chronic active gastritis), and other forms of gastrointestinal inflammation caused by an infectious agent, and other like conditions.

Acute and chronic inflammation is secondary to an increase in pro-inflammatory cytokines (e.g., tumor necrosis factor-alpha) and an increase in epithelial cell apoptosis. The resultant manifestations of these factors are a loss of the mucosal epithelial lining and neutrophil/monocyte infiltrate.

As used herein, "inflammatory bowel disease" or "IBD" refers to any of a variety of diseases characterized by inflammation of all or part of the intestines. Examples of inflammatory bowel disease include, but are not limited to, Crohn's disease, ulcerative colitis, irritable bowel syndrome, mucositis, radiation induced enteritis, short bowel syndrome, celiac disease, colitis, stomach ulcers, diverticulitis, pouchitis, proctitis, and chronic diarrhea. Reference to IBD throughout the specification is often referred to in the specification as exemplary of gastrointestinal inflammatory conditions, and is not meant to be limiting.

As used herein, the terms "symptoms of IBD" "signs of IBD" and "signs and symptoms of IBD" refer to detected signs and/or symptoms such as abdominal pain, diarrhea, rectal bleeding, weight loss, fever, loss of appetite, and other more serious complications, such as dehydration, anemia and malnutrition. A number of such signs and symptoms are subject to quantitative analysis (e.g. weight loss, fever, anemia, etc.). Some signs and/or symptoms are readily determined from a blood test (e.g. anemia) or a test that detects the presence of blood (e.g. rectal bleeding). The term "wherein said signs and/or symptoms are reduced" and the like refer to a qualitative or quantitative reduction in detectable symptoms, including but not limited to a detectable impact on the rate of recovery from disease (e.g. rate of weight gain). Diagnosis is typically determined by way of an endoscopic observation of the mucosa, and pathologic examination of endoscopic biopsy specimens.

As used herein, the phrase "under conditions such that the signs and/or symptoms are reduced" and the like refer to any degree of qualitative or quantitative reduction in detectable symptoms of disease (e.g., IBD), including but not limited to, a detectable impact on the rate of recovery from disease (e.g. rate of weight gain), or the reduction of at least one of the following symptoms: abdominal pain, diarrhea, rectal bleeding, weight loss, fever, loss of appetite, dehydration, anemia, distention, fibrosis, inflamed intestines and malnutrition.

As used herein, the terms "at risk for IBD" "subject at risk for IBD" and the like refer to the segment of the world population that has an increased risk (e.g., over the average person) for IBD and can occur at any age. IBD occurs worldwide, but is most common in the United States, England, and northern Europe. IBD is especially common in people of Jewish descent. An increased frequency of this condition has been recently observed in developing nations. Increased risk is also most prevalent in people with family members who suffer from IBD.

As used herein, the term "therapeutic composition comprising one or more AT1a antagonists" or functional equivalents thereof refer to compositions containing one or more AT1a antagonists (e.g., chemical and/or other type of therapeutic that antagonizes At1a signaling) that may additional contain one or more other compounds or agents including, but not limited to, ACE inhibitors, therapeutic agents, physiologically tolerable liquids, gels, carriers, diluents, adjuvants, excipients, salicylates, steroids, immunosuppressants, antibodies, cytokines, antibiotics, binders, fillers, preservatives, stabilizing agents, emulsifiers, and/or buffers.

As used herein, the term "continuous manner" when used in reference to the method of delivery or administration of the therapeutic composition comprising AT1a antagonists of the present invention refers to a substantially uninterrupted administration such that a therapeutic dosage is stretched over a period of time and avoids dosage spiking that is common among other modes of administration (e.g. oral administration or intravenous administration). Examples of modes of administration that employ a continuous manner of delivery include, but are not limited to, a suppository, or a slow release oral formulation.

As used herein, the term "subject" refers to a patient that is administered the therapeutic composition comprising ACE inhibitors of the present invention. Examples of subjects, include, but are not limited to, humans and other mammals such as non-human primates, horses, dogs, and cats.

As used herein, the terms "host," "subject" and/or "patient" refer to any animal, including but not limited to, human and non-human animals (e.g. rodents, arthropods, insects (e.g., Diptera), fish (e.g., zebrafish), non-human primates, ovines, bovines, ruminants, lagomorphs, porcines, caprines, equines, canines, felines, aves, etc.), that is studied, analyzed, tested, diagnosed or treated. As used herein, the terms "host," "subject" and "patient" are used interchangeably.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "effective amount" refers to the amount of a composition (e.g., comprising one or more AT1a antagonists) sufficient to effect beneficial or desired results. An effective amount can be administered in one or more administrations, applications or dosages on one or more different days and is not intended to be limited to a particular formulation or administration route.

As used herein, the terms "administration," "administering" and functional equivalents refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), enteric administration (e.g., via the mouth (oral) or rectally), skin (transdermal), nose (nasal), lungs (inhalant), oral mucosa (buccal), ear, rectal, intestine (enteral), by injection (e.g., intravenously, subcutaneously, intratumorally, intraperitoneally, etc.) and the like.

As used herein, the terms "co-administration," "co-administering" and functional equivalents refer to the administration of at least two agent(s) (e.g., a composition comprising an AT1a antagonist and one or more other agents—e.g., a steroid) or therapies to a subject. In some embodiments, the co-administration of two or more agents or therapies is concurrent. In other embodiments, a first agent/therapy is administered prior to a second agent/therapy. Those of ordinary skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., inflammatory bowel disease). A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., inflammatory bowel disease) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (e.g., malnutrition, industrial hazards, or climate), to specific infective agents (e.g., worms, bacteria, or viruses), to inherent defects of the organism (e.g., genetic anomalies), and/or combinations of these and other factors.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., inflammatory bowel disease).

"Short Bowel Syndrome" refers to the condition of the gastrointestinal tract whereby the bowel is lacks an adequate length to allow for the sufficient length to absorb nutrients, fluids and/or electrolytes.

"Intestinal failure" refers to the condition of a gastrointestinal tract which lacks sufficient ability to absorb nutrients, fluids and electrolytes to sustain an organism, and to provide for growth. The condition includes, but is not limited, to conditions of short bowel syndrome, malabsorption, overwhelming inflammatory conditions of the bowel, and dymotility syndromes (conditions whereby the bowel lacks adequate mobility to propel nutrients through the intestine).

As used herein, the term "substituted aliphatic" refers to an alkane possessing less than 10 carbons where at least one of the aliphatic hydrogen atoms has been replaced by a halogen, an amino, a hydroxy, a nitro, a thio, a ketone, an aldehyde, an ester, an amide, a carboxy, a sulfonamide, a sulfone, a sulfoxide and an alkoxy, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of no more than three fused rings at least one of which is aromatic, and where at least one of the hydrogen atoms on a ring carbon has been replaced by a halogen, an amino, a hydroxy, a nitro, a thio, a ketone, an aldehyde, an ester, an amide, a lower aliphatic, a substituted lower aliphatic, or a ring (e.g., aryl, substituted aryl, cycloaliphatic, or substituted cycloaliphatic). Examples of such include, but are not limited to, hydroxyphenyl and the like.

As used herein, the term "cycloaliphatic" refers to a cycloalkane possessing less than 8 carbons or a fused ring system consisting of no more than three fused cycloaliphatic rings.

As used herein, the term "substituted cycloaliphatic" refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (e.g., aryl, substituted aryl, cycloaliphatic, or substituted cycloaliphatic). Examples of such include, but are not limited to, 1-chlorodecalyl and the like.

As used herein, the term "heterocyclic" refers to a cycloalkane and/or an aryl ring system, possessing less than 8 carbons, or a fused ring system comprising no more than three fused rings, where at least one of the ring carbon atoms is replaced by oxygen, nitrogen or sulfur. Examples of such include, but are not limited to, morpholino and the like.

As used herein, the term "substituted heterocyclic" refers to a cycloalkane and/or an aryl ring system, possessing less than 8 carbons, or a fused ring system comprising no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (e.g., aryl, substituted aryl, cycloaliphatic, or substituted cycloaliphatic). Examples of such include, but are not limited to 2-chloropyranyl.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "acetylamino" shall mean any primary or secondary amino that is acetylated. Examples of such include, but are not limited to, acetamide and the like.

The term "derivative" of a compound, as used herein, refers to a chemically modified compound wherein the chemical modification takes place either at a functional group of the compound and/or on an aromatic ring (e.g., to make the compound (e.g., AT1a receptor antagonist) less cell permeable and/or less absorbable).

As used herein, the expression "acyl" can denote a $C_{1-20}$ acyl residue, preferably a $C_{1-8}$ acyl residue and especially preferred a $C_{1-4}$. acyl residue; "cycloalkyl" can denote a $C_{3-12}$. cycloalkyl residue, preferably a $C_4$, $C_5$ or $C_6$ cycloalkyl residue; and "a carbocycle" can denote a $C_{3-12}$ a carbocycle residue, preferably a $C_4$, $C_5$ or $C_6$ a carbocycle residue. "Heteroaryl" is defined as an aryl residue, wherein 1 to 4, and more preferably 1, 2 or 3 ring atoms are replaced by heteroatoms like N, S or O. "A heterocycle" is defined as a cycloalkyl residue, wherein 1, 2 or 3 ring atoms are replaced by heteroatoms like N, S or O.

As used herein, the expression "alkyl" can denote a $C_{1-50}$ alkyl group, preferably a $C_{1-30}$ alkyl group, especially a $C_{1-8}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms; the expression "alkenyl" can denote a $C_{2-10}$ alkenyl group, preferably a $C_{2-6}$ alkenyl group, which has the double bond(s) at any desired location and may be substituted or unsubstituted; the expression "alkynyl" can denote a $C_{2-10}$ alkynyl group, preferably a $C_{2-6}$ alkynyl group, which has the triple bond(s) at any desired location and may be substituted or unsubstituted.

The expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the afore-mentioned substituents may in turn have one or more alkyl, alkenyl, alkynyl, mono- or multi-valent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae $(alkyl)_{2N}$- or alkyl-NH—, —CO—N(alkyl)$_2$. or —CO—NH(alkyl), -alkyl-OH or -alkyl-COOH. Furthermore, the expression "substituted" or "substituent" can denote one or two of each, branched or unbranched alkyl chain, a branched or unbranched alkenyl chain, a branched or unbranched alkynyl chain, a carbocycle, aryl, heteroaryl, a heterocycle; the afore-mentioned substituents may in turn have one or more branched or unbranched alkyl chain, a branched or unbranched alkenyl chain, a branched or unbranched alkynyl chain, a carbocycle, aryl, heteroaryl, a heterocycle as side group(s); all herein before mentioned chains, residues or side groups may contain one or more, preferably one or two, epoxy moiety(ies) and one or more, preferably one or two, substituted or unsubstituted aziridine(s), whereas the substitution is characterized as $R_1$ which is described above; all chains, residues or side groups may be substituted by one or more F, Cl, Br, I, $NH_2$, NO, $NO_2$, CN atoms or groups, isocyanide(s), cyanate(s), isocyanate(s), fulminate(s), thiocyanate(s), isothiocyanate(s), selenocyanate(s) and isoselenocyanate(s), thio acids of sulphur with empirical formulae —$S_2H$, —$S_2OH$, —$S_3H$, —$S_2O_2H$, —$S_3OH$, and —$S_4H$ and their derivatives, whereas the substitution is characterized as $R_1$; azonic acid(s), azinic acid(s), sulphonic acid(s) ($SO_2H$), sulphur acid(s) ($SO_3H$) and their esters, whereas the ester residue(s) is characterized as $R_1$; phosphinous acid(s), phosphonous acid(s), phosphinic acid(s), phosphonic acid(s), their replaced modifications like phosphinothioic O-acid(s), phosphinothioic S-acid(s), phosphinimidic acid(s), phosphonothioic O,O'-acid(s), phosphonothioic O,S'-acid(s), phosphonimidothioic acid(s) and their esters, whereas the ester residue(s) is characterized as $R_1$.

Furthermore, all afore-mentioned chains, residues or side groups may contain one or more alcohol(s), acid(s), aldehyde(s) or ketone(s), phosphane(s), phosphorane(s), sulfoxides (SO), sulfones ($SO_2$), their selenium or tellurium analogues named selenoxide and selenone, sulfonic anhydride(s) (($SO_2$)$_2$O) and sulphonic anhydride(s) (($SO$)$_2$O), hydrazide(s), N-Oxides of azo compounds; as well as amine(s), amide(s), ester(s), ether(s) or sulfonamid(e), phosphane(s) or phosphorane(s), having the formula —$NHR_1$ or —$N(R_1)_2$, —$CON(R_1)_2$. or —$CONHR_1$, —$CO—OR_1$, $R_1$—$O$—$R_1$, —$SO_2N(R_1)_2$. or —$SO_2NHR_1$, —$PHR_1$, —P($R_1$)$_2$, —PH$_3$$R_1$, —PH$_2$($R_1$)$_2$, —PH($R_1$)$_3$, —P($R_1$)$_4$, whereas $R_1$. is described above; as well as the corresponding thio analogues of the above described residues, where the oxygen is replaced by sulphur, for example thiol(s), thioaldehyde(s) and thioketone(s).

Amino acids which can be used in the present invention are L and D-amino acids, N-methyl-amino acids, aza-amino acids; allo- and threo-forms of Ile and Thr, which can, e.g. be α-, β- or o-amino acids.

Examples of amino acids include aspartic acid (Asp), glutamic acid (Glu), arginine (Arg), lysine (Lys), histidine (His), glycine (Gly), serine (Ser), cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-aminooctanoic acid (Aoa), acetidine-(2)-carboxylic acid (Ace), pipecolic acid (Pip), 3-aminopropionic acid, 4-aminobutyric acid and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic acids. Examples of .omega.-amino acids are e.g.: 5-Ara (aminoraleric acid), 6-Ahx (aminohexanoic acid), 8-Aoc (aminooctanoic acid), 9-Anc (aminovanoic acid), 10-Adc (aminodecanoic acid), 11-Aun (aminoundecanoic acid), 12-Ado (aminododecanoic acid). Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal) and (2-Nal), 4-aminophenylalanine (Phe(4-NH.sub.2)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe (3,4-Cl.sub.2)), 3-fluorophenylalanine (Phe(3-F)), 4-fluorophenylalanine (Phe(4-F)), 3,4-fluorophenylalanine (Phe(3,4-F.sub.2)), pentafluorophenylalanine (Phe(F.sub.5)), 4-guanidinophenylalanine (Phe(4-guanidino)), homophenylalanine (hPhe), 3-jodophenylalanine (Phe(3-J)), 4-jodophenylalanine (Phe (4-J)), 4-methylphenylalanine (Phe(4-Me)), 4-nitrophenylalanine (Phe-4-NO.sub.2)), biphenylalanine (Bip), 4-phosphonomethylphenylalanine (Pmp), cyclohexylglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3, 5-J.sub.2)), methyltyrosine (Tyr(Me)), 2',6'-dimethyltyrosine (Dmt), 3-NO.sub.2-tyrosine (Tyr(3-NO.sub.2)), phosphotyrosine (Tyr(PO.sub.3H.sub.2)), alkylglycine, 1-aminoindane-1-carboxylic acid, 2-aminoindane-2-carboxylic acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly(NH.sub.2)), diaminobutyric acid (Dab), 1,3-dihydro-2H-isoinole-carboxylic acid (Disc), homocylcohexylalanine (hCha), homophenylalanine (hphe or Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), .beta.-(2-thienryl)-alanine (Tha).

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

DETAILED DESCRIPTION OF THE INVENTION

The present invention provides compositions and methods for treating inflammatory conditions (e.g., of the bowel). In particular, the present invention provides methods of treating (e.g., therapeutically and/or prophylactically treating) inflammatory conditions (e.g., of the bowel), compositions useful for such methods (e.g., antagonists and/or inhibitors of angiotensin II (AngII) receptor Type 1a (AT1a)), and methods of identifying, characterizing and/or optimizing such compositions. Compositions and methods of the present invention find use in, among other things, clinical (e.g. therapeutic and preventative medicine) and research applications.

For example, in some embodiments, the present invention provides compositions and methods for treating and/or preventing inflammatory bowel disease and/or intestinal fibrosis associated with inflammatory bowel disease, as well as other gastrointestinal inflammatory disorders and disorders which may promote the development of intestinal fibrosis. In some embodiments, the present invention provides compositions and methods for treating and/or preventing pulmonary fibrosis. In some embodiments, the present invention provides compositions and methods for treating and/or preventing inflammatory processes and fibrosis of the genitourinary system, connective tissues, central nervous system, peripheral nervous system, muscles, joint spaces, liver, biliary tree, cardiovascular system, or other portions of the airway that may develop an inflammatory or fibrotic process. For example, in some embodiments, the present invention provides compositions and methods of treating and/or preventing disorders via the delivery (e.g., local delivery) of compositions comprising antagonists to the angiotensisn II (Ang II) type 1a (AT1a) receptor.

The renin angiotensin system (RAS) is one of the most powerful regulators of blood pressure and volume homeostasis in mammals. Its effector peptide angiotensin II (Ang II) is cleaved from the decapeptide angiotensin I by the metalloprotease ACE (See, e.g., Benigni et al., J Cardiovasc Pharmacol. 2000; 35(4 Suppl 2):S75-78; Wolny et al., Circ. Res. 1997, 80, 219-227). ANG II mediates all the effects of RAS after binding to its G-protein-coupled angiotensin II type 1 (AT1) receptor and thus plays a complex role in the regulation of blood pressure, fluid, and electrolyte homeostasis. More recently, Ang II was shown to regulate vascular tone by delayed effects on vascular smooth muscle via growth stimulation, aldosterone production, and release, leading to increased salt absorption in the kidney and gut and the induction of thirst and sodium appetite in the brain. It also stimulates the release of vasopressin, luteinizing hormone, oxytocin, and corticotropin. Ang II further induces vagus suppression and β-adrenergic potentiation and increases inotropy and chronotropy. Ang II stimulates synthesis of prostaglandin (See, e.g., Mayer, J. Pharmacol. Exp. Ther. 1996, 279, 633-644), endothelin (See, e.g., Beckman et al., Proc. Natl. Acad. Sci. U.S.A. 1990, 87, 1620-1624), and elicits procoagulatory effects by activating the plasminogen activator (PA) plasmin system (See, e.g., Wong et al., J. Pharmacol. Exp. Ther. 1990, 252, 719; Raij et al., Kidney Int. 1995, 48, 20-32; Pollman et al., Circ. Res. 1996, 79, 748-756; and Kagami et al., J. Clin. Invest. 1994, 93, 2431-2437). Thus, inhibition of RAS and that of the AT1 receptor have been utilized to control blood pressure and vascular maladaptive processes in an effort to prevent cardiovascular diseases.

Thus, one role of Ang II is to act as a pro-inflammatory mediator and growth factor, much like the pro-inflammatory cytokines (See, e.g., Phillips et al., Curr Opin Investig Drugs. 2002 April; 3(4):569-77). Ang II exerts most of its physiological effects via the angiotensin type 1 receptor (AT1, with subtypes 1a and 1b). Stimulation of the AT1a receptor leads to activation of NF-κB, and subsequent nuclear transcription of TNF-α and other proinflammatory cytokines (See, e.g., McAllister-Lucas et al., Proc Natl Acad Sci USA. 2007 Jan. 2; 104(1):139-44).

The NF-κB pathway exists as a major signaling pathway by which TNF-α, IL1β, and IL-6 are expressed, classically via TNF-α. Upon appropriate cell surface stimulation, the NF-κB system is activated via a protein kinase C-dependent system. This stimulation causes I-κB to undergo phosphorylation and ubiquination, which subsequently releases NF-κB, allowing it to translocate to the nucleus for transcription of these pro-inflammatory cytokines (See, e.g., Hayden et al., Oncogene. 2006 Oct. 30; 25(51):6758-80). Elimination of I-κB control over NF-κB, by ablating NEMO (I-κB-κ kinase), results in severe chronic intestinal inflammation (See, e.g., Davé et al., J. Immunol. 2007 Dec. 1; 179(11): 7852-9), and delivery of NEMO-binding domain peptide can prevent NF-κB activation (See, e.g., Nenci et al., Nature. 2007 Mar. 29; 446(7135):557-61). Thus, NF-κB activation in the gut epithelium exists as a critical regulator of intestinal immune homeostasis.

A beneficial effect of a chronic RAS blockade was first shown for inhibitors of the angiotensin converting enzyme (ACE), such as captopril, quinapril, enalapril, and ramipril in patients with ischemic heart disease, congestive heart failure, and postmyocardial infarct (MI) in a variety of large-scale clinical trials. Although ACE inhibitors were the only drugs available up to 1995 that interfered with the RAS, it was recognized that other enzymes such as chymase CAGE, cathepsin G, tPA, elastase tonin, and others also generate ANG II. Moreover, ACE is identical to kininase II, an enzyme that degrades bradykinin and other kinins to inactive metabolites. A blockade of ACE is therefore associated with a potentiation of endogenous kinins, a mechanism thought to contribute to desirable effects of ACE inhibitors such as organ protection, but also associated with unwarranted effects such as dry cough.

The development of drugs that interfered with the RAS: the angiotensin receptor type 1 (AT1) antagonists began in the mid-1980s (See, e.g., Duncia et al., Med. Res. Rev. 1992, 12, 149-191; Duncia et al., J. Med. Chem. 1990, 33, 1312-1329). To find a more specific blockade of ANG II at its AT1 receptor, highly selective non-peptidic AT1-receptor antagonists were designed and developed as competitive antagonists with virtually no agonistic effect at the receptor level. Losartan was described as the first non-peptide AT1 receptor antagonist (e.g., the first member of the sartan family). There are additional compounds commercially available and in development. In general, these compounds share the biphenyltetrazole unit or replacements thereof with the original, advanced lead losartan (See, e.g., Israili, J. Hum. Hypertens. 2000, 14 (Suppl. 1), S73-S86).

The sartans are metabolized by enzymatic oxidation by the cyclochrome P450 family and/or glucoronidation by UDP-glucoronyl transferases. Usually this metabolism results in reduced AT1 affinity and potency. The ratio of renal to liver clearance varies significantly for the drugs, and large species-dependent differences have been observed, but liver clearance is a dominant path for elimination.

In some embodiments, the present invention provides antagonists and/or inhibitors of AT1a (e.g., derivatives and/or analogs of AT1a antagonists (e.g., sartans)). The present invention is not limited to any particular AT1a antagonist and/or inhibitor. Indeed, a variety of AT1a antagonists and/or inhibitors described herein find use in the present invention. In some embodiments, the present invention provides compositions comprising one or more AT1a antagonists and/or inhibitors, wherein the antagonist and/or inhibitor lacks (e.g., displays little to no) cell permeability and/or absorbability (e.g., lacks (e.g., displays little to no) plasma permeability (e.g., has poor enteral absorption when administered to the GI tract)). For example, in some embodiments, the present invention provides a composition comprising an AT1a antagonist or derivative thereof that shows little to no cellular permeability and/or that displays low to no presence in the circulatory system (e.g., blood concentration level) of a subject administered the composition comprising the AT1a antagonist or derivative thereof.

In some embodiments, the present invention provides one or more derivatives of an AT1a receptor antagonist and/or inhibitor (e.g., a sartan derivative and/or analogue (e.g., wherein the one or more derivatives display little to no cell (e.g., plasma) permeability and/or absorbability)). Although an understanding of a mechanism is not necessary to practice the present invention, and the present invention is not limited to any particular mechanism of action, in some embodiments, administration of a composition of the present invention (e.g., comprising an AT1a antagonist derivative that is non-cell permeable/absorbable (e.g., lacks plasma permeability (e.g., has poor enteric/enteral absorption when given into the GI tract)) exerts its effects only locally (e.g., at the site of administration (e.g., in the intestine) rather than distally (e.g., due to lack of membrane permeability)).

The present invention provides compounds that antagonize/inhibit the AT1a receptor of Ang II. Thus, in some embodiments, the present invention provides compounds that have high efficacy in the treatment and prevention of inflammatory diseases of the gastrointestinal tract including conditions of gastrointestinal fibrosis and epithelial cell apoptosis (cell death). Compositions and methods of the present invention find use in the treatment and/or prevention of inflammatory bowel diseases including, but not limited to, Crohn's disease, ulcerative colitis, indeterminate colitis, gastritis, proctitis, and pouchitis. The present invention provides compounds that act as AT1a antagonists and/or inhibitors, and methods of generating, characterizing and/or identifying the same, that have or that are designed to have low to undetectable cell membrane permeability and/or low to undetectable gastrointestinal absorption (e.g., thereby leading to low or undetectable concentrations of the analogs in the systemic circulation of a subject administered a composition comprising the AT1a antagonist derivative and/or anaolog). Thus, the present invention provides for the delivery and/or administration (e.g., local delivery/administration) of high doses (e.g., at or exceeding the parenteral dosing of an identical AT1a antagonist (e.g., 2 times (x), 4x, 8x, 10x, 20x, 40x, 50x, 60x, 70x, 80x, 90x, 100x, 250x, 500x, 1000x or more than a parenteral dose of an AT1a antagonist) of an AT1a antagonist and/or derivative or analogue thereof provided herein (e.g., allowing for increased efficacy and resulting in little to no systemic side-effects (e.g., a decline in intestinal blood flow or decline in systemic blood pressure)).

For example, in some embodiments, the present invention provides analogs and/or derivatives that are related structurally to the AT1a antagonist losartan and/or analogs and/or derivatives that are related structurally to the AT1a antagonist candesartan (See, e.g., Example 1). In some embodiments, the analogs and/or derivatives of losartan and/or analogs and/or derivatives of candesartan possess structural modifications/attributes that render the molecules highly impermeable to cell membranes (e.g., epithelial cell membranes and/or cell membranes of vasculature adjacent to epithelial cells). Although an understanding of a mechanism is not needed to practice the present invention, and the present invention is not limited to any particular mechanism of action, in some embodiments, the administration (e.g., to a subject with disease (e.g., inflammatory disease (e.g., intestinal inflammatory disease))) of AT1a antagonist analogs and/or derivatives (e.g., with little to no detectable cell membrane permeability) provided herein limits the analogs' exposure in vivo to the site of administration (e.g., to the intestine alone) and/or confines the action of the analogue/derivative to a localized body cavity and/or space.

The present invention is not limited to derivatives and/or analogues of losartan and candesartan. Indeed, derivatives and analogues of other AT1a antagonists find use in the present invention including, but not limited to, azilsartan, eprosartan, irbesartan, valsartan, olmesartan, telmisartan and tasosartan. In some embodiments, active metabolites of AT1a antagonists, as well as derivatives or analogues thereof, conjugates, and other related compounds also find use in the compositions and methods of the present invention.

Figure 2:
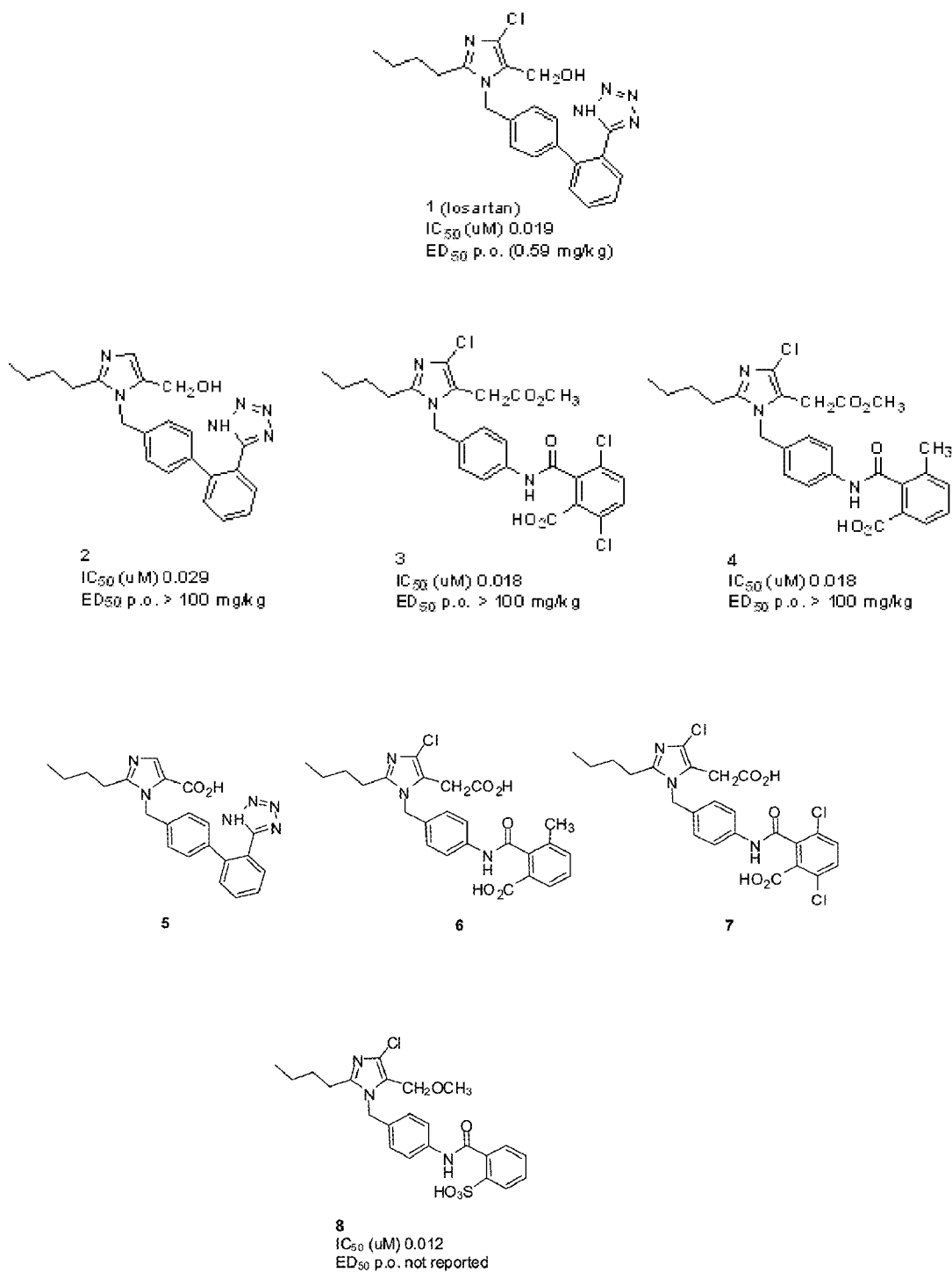
FIG. 2 shows losartan and several examples of derivatives thereof.

In some embodiments, the present invention provides analogs configured for minimal absorption from the intestinal tract into the systemic circulation. For example, in some embodiments, information generated during structure-activity relationship (SAR) characterization generated during the development of losartan is utilized to generate analogs and/or derivatives (See, e.g., Duncia et al., Med Res Rev. 1992 March; 12(2):149-91; Duncia et al., Med Chem 1990 33: 1312-1329; J Med. Chem. 1991 August; 34(8):2525-47). Several structural features of losartan were discovered to be key to achieving its robust oral activity, including the chloro and hydroxyl groups on the imidazole, and the tetrazole on the biphenyl. If the chloro group is not present, the resulting molecule lacks oral activity (e.g., See FIG. 2, compound 2) while maintaining nearly the same receptor blockade function as losartan. The hydroxyl and tetrazole groups of losartan each replaced carboxylic acids present in earlier analogs and were subsequently found to augment oral activity, presumably due to their reduced polarity and negative charge at physiological pH. In some circumstances, polar surface area is inversely correlated with cell permeability and oral bioavailability (See, e.g., Veber et al., J Med. Chem. 2002 Jun. 6; 45(12):2615-23). For example, early analogs of losartan that contain carboxylic acids in the "southern" region of the molecule lack oral activity (See, e.g., Compounds 3 and 4 in FIG. 2). Published SAR indicates that a carboxylic acid moiety on the imidazole, or on the distal phenyl ring in the "southern" region of the molecule, contributes to AT1a binding affinity. Thus, in some embodiments, the present invention provides derivatives and/or analogs of losartan that contain one or more charged moieties (e.g., an acidic moiety (e.g., carboxylic acid, sulfonic acid and/or other moiety)) at the imidazole and/or on the distal phenyl ring in the "southern" region of the molecule (e.g., that reduces and/or eliminates oral activity and/or augments binding activity). For example, compound 5 of FIG. 2 has a reported $IC_{50}$ against the binding of Ang II to the AT1a receptor of 2.9 nM, a full order of magnitude better than losartan (50 nM) in the same assay (See, e.g., Taylor, 1994). In some embodiments, the present invention provides a derivative and/or analog of a sartane (e.g., losartan) that is highly charged at physiological pH (e.g., that displays resistance to passive permeation into cells). For example, a composition comprising compound 8 of FIG. 2 which incorporates a highly acidic sulfonic acid moiety in place of the carboxylic acids of related compounds 3 and 4 is utilized in the compositions and methods of the present invention.

Figure 3:
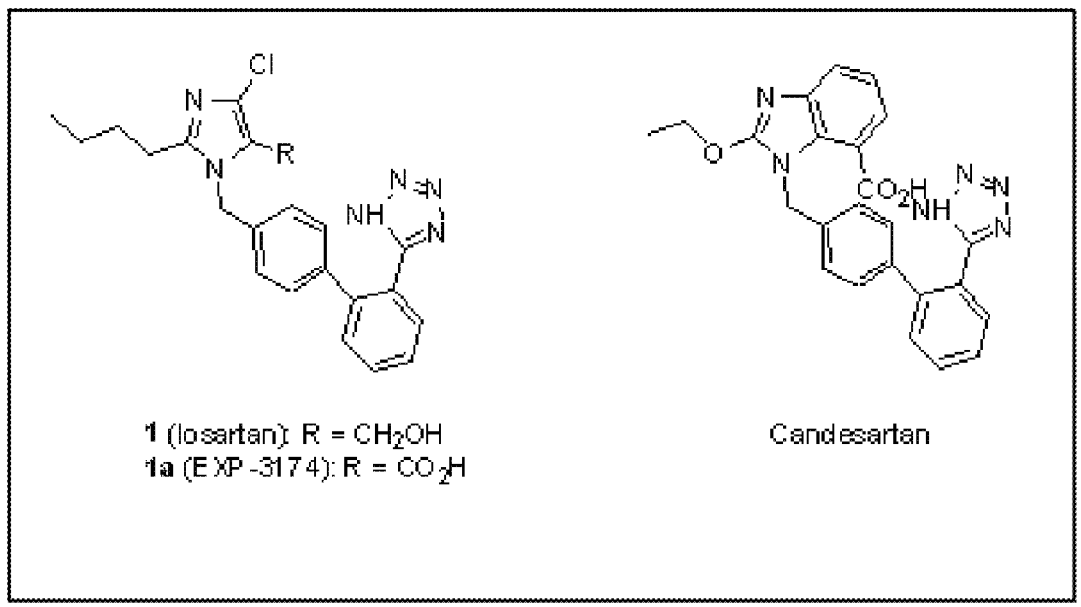

In some embodiments, the present invention provides analogs and/or derivatives (e.g., of a sartane (e.g., losartan, candesartan, etc.)) with two or more acidic functionalities (e.g., diacid, triacid, etc.) that provide even more complete impermeability and/or lack of intestinal absorption (e.g., leading to a longer duration of action at the site of administration). For example, it has been observed that some AT receptor antagonists have slower ligand-receptor dissociation constants, displaying longer durations of action against, and significantly attenuated maximal responses to, subsequently administered Ang II (See, e.g., Vauquelin et al., Trends Pharmacol Sci. 2001 July; 22(7):343-4). This phenomenon, termed "insurmountable" antagonism, tends to be associated with structures possessing two negatively charged (acidic) functionalities, and is postulated to result from the formation of a tight-binding ligand-receptor complex arising from two strong charge-charge interactions with positively charged (basic) residues lining the binding site. An illustrative example is provided by a comparison of the in vitro and in vivo durations of action of losartan (shown as compound 1 in FIG. 3) and its diacid metabolite EXP-3174 (shown as compound 1 in FIG. 3). The half-life for release of monoacid 1 from the AT1 receptor is only 5 minutes, compared with 31 minutes for the corresponding diacid 1 (See, e.g., Unger et al., Blood Press Suppl. 2001; (3):5-10). When administered intravenously (i.v.) to Ang I-infused dogs at a dose of 1 mg/kg, monoacid 1 maintained a ≧20 mmHg drop in mean arterial blood pressure (MABP) for only 30 min, whereas diacid 1 maintained the same reduction in MABP for nearly 3 h (See, e.g., Brooks, J Pharmacol Exp Ther. 1992 November; 263(2):422-7). The longest reported "insurmountable" antagonism is displayed by candesartan (shown in FIG. 3) 152 min half-life for ligand-receptor dissociation (See, e.g., Unger, Blood Press Suppl. 2001 (3):5-10).

AT1a antagonist and/or derivatives and/or analogues of the present invention may be used alone or in combination with any other known or later identified treatment or intervention for inflammation diseases (e.g., gastrointestinal inflammatory conditions (e.g., IBD)). In some embodiments, the present invention provides new compositions and methods for using antagonists to AT1a receptors in the treatment and prevention of such conditions. The AT1a antagonists of the present invention may be used alone, or in combination with any other known or later identified treatment or intervention for such conditions.

For example, in some embodiments, the present invention provides a composition comprising an AT1a antagonist derivative and/or analog further comprising one or more angiotensin converting enzyme (ACE) inhibitors (e.g., for the therapeutic and/or prophylactic treatment of inflammatory disease (e.g., inflammatory bowel disease)). Thus, the present invention provides compositions and methods for using AT1a antagonist derivatives and/or analogues (e.g., alone or in combination with other agents (e.g., ACE inhibitors)) in the treatment and prevention of such conditions. In some embodiments, a composition comprising an AT1a antagonist derivative and/or analogue is utilized with an ACE inhibitor described in U.S. Patent Application Publication No. 20070123499, hereby incorporated by reference in its entirety for all purposes.

Examples of ACE inhibitors that find use in the compositions and methods of the present invention include, but are not limited to, Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); R.sub.O 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxy-carbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983), each of which is hereby incorporated by reference in its entirety.

In some embodiments, AT1a antagonists alone or in combination with other drugs may be incorporated in a single conventional dosage form or each compound may be incorporated into a separate conventional dosage form to be taken at the same time. The dosage forms may comprise conventional enteric formulations (e.g., oral forms, rectal forms or forms for transanal administration) or parenteral forms, such as tablets, capsules, suppositories, enemas, powders, ampoules, elixirs, suspensions, solutions, syrups, and sustained release preparations. The dose administered may be adjusted according to age, weight and condition of the patient, as well as the route of administration, dosage form and regimen and the desired result.

In some embodiments, an AT1a antagonist or derivative thereof is administered to a subject (e.g., a human subject) in an amount within the range of from about 0.01 mg/kg to about 100 mg/kg, although higher and lower doses may be utilized. For example, in some embodiments, between about 100-200, 200-400, 400-800, or 800-1000 mg/kg or more of an AT1a antagonist or derivative thereof is administered. In some embodiments, about 10 mg/kg is administered in a dose. Compositions and methods of the present invention permit dosing of a greater degree than for non derivatized antagonists. For example, compositions and methods of the present invention permit better local antagonism due to poor to undetectable absorption of the analogs/derivatives, with little to no detectable systemic distribution of the compound.

In some embodiments, an oral dosage form, such as tablets or capsules, contain an AT1a antagonist from about 100 to about 5000 mg, preferably from about 500 mg to about 1000 mg. Tablets of various sizes can be prepared, e.g., of about 50 to 1000 mg in total weight, containing one or more active substances (e.g., in the ranges described above) with the remainder being a physiologically acceptable carrier of other materials according to accepted pharmaceutical practice. In some embodiments, tablets are scored to provide for fractional doses. Gelatin capsules can be similarly formulated.

In some embodiments, the present invention provides a composition comprising an AT1a antagonist/inhibitor or derivative thereof and polyethylene glycol (e.g., of 1000-1500 molecular weight). In further embodiments, a composition comprising an AT1a antagonist/inhibitor or derivative thereof is suspended in a relatively non-inert polyethylene glycol carrier (e.g., 1000-1500 molecular weight). This composition can be directly delivered to a subject (e.g., via rectal or oral administration). Additionally, in some embodiments, the composition comprising an AT1a antagonist/inhibitor or derivative thereof and polyethylene glycol may comprise one or more other agents (e.g., ACE inhibitor, steroid (e.g. prednisone), etc.). In some embodiments, direct administration to a subject rectally via an enema circumvents systemic immunosuppression accompanied with systemic administration of steroids.

Although an understanding of the mechanism is not necessary to practice the present invention and the present invention is not limited to any particular mechanism of action, a composition comprising a derivative and/or analogue of an AT1a antagonist/inhibitor provided herein is configured for reduced absorption of the composition. Certain types of AT1a antagonists/inhibitors as well as agents co-administered with AT1a antagonists can be selected for use in the compositions and methods of the present invention based on their inability to be absorbed by healthy mucosa, thereby providing increased specificity of the compositions and methods. For example, the ACE inhibitor enalaprilat can be selected as an additional agent to be co-administered with an AT1a antagonist/inhibitor because it is not normally absorbed through mucosa which is non-inflamed and intact. Thus, in some embodiments, a composition comprising an AT1a antagonist/inhibitor with or without polyethylene glycol and/or an ACE inhibitor is administered directly onto the inflamed mucosal lining (e.g., it is not administered systemically).

Compositions and methods of the present invention provide a minimal systemic immunosuppressive effect. Specifically, the direct administration of a composition of the invention to the gastrointestinal tract avoids many of the adverse systemic effects of current agents. For example, one of the advantages in the use of an AT1a antagonist/inhibitor derivative or analog with low to undetectable cell permeability, in general, for the treatment of inflammatory bowel disease is that this agent lacks systemic immunosuppressive properties, properties that are inherent in medicines currently used for inflammatory bowel disease (e.g., steroids).

The present invention further provides a method of treating a subject with inflammatory bowel disease comprising administering to the subject a composition comprising AT1a antagonist/inhibitor, and co-administering one or more steroids (e.g., prednisone). In some preferred embodiments, co-administration of these compositions reduces the dose of steroid (e.g., prednisone) required to provide a beneficial effect (e.g., the dose of steroid is lower than in conventional treatments using the steroid independently).

Treatment of the various intestinal bowel diseases and disorders described herein are often generally limited by the following two major factors: (1) the development of drug resistance and (2) the toxicity of known therapeutic agents (e.g., systemic immunosuppression associated with systemic administration of steroids). Some therapeutic agents have deleterious side effects, including non-specific lymphotoxicity and renal toxicity.

The methods described herein address both these problems. Drug resistance, where increasing dosages are required to achieve therapeutic benefit, is overcome by co-administering the compounds comprising an AT1a antagonist/inhibitor described herein with the known agent (e.g., steroid, ACE inhibitor, anti-cytokine therapy, azulfidine, etc.). In some embodiments, the compounds described herein sensitize target cells (e.g., colonic mucosal epithelial cells) to known agents (and vice versa) and, accordingly, less of these agents (e.g., steroids) are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. Thus, in some embodiments, when the claimed compounds are co-administered with the known agent, they reduce the dosage required which, in turn, reduces the deleterious effects. Further, because the claimed compounds are themselves both effective and non-toxic, co-administration of proportionally more of these compounds than known toxic therapeutics will achieve the desired effects while minimizing toxic effects (See, e.g., FIGS. 11-13).

Figure 11:
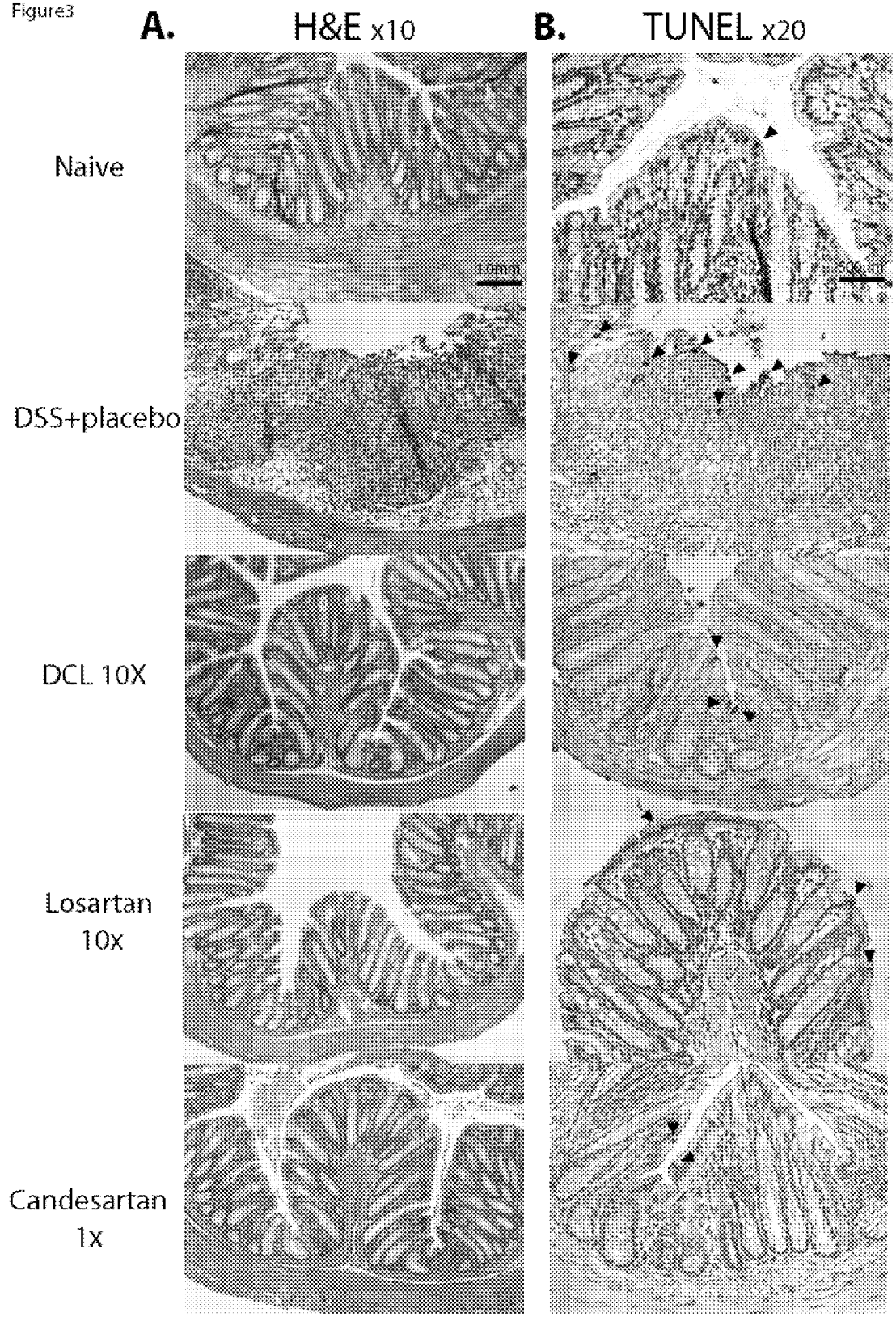
FIG. 11 shows A) Representative histologic sections of distal colon after undergoing Hematoxilyn-Eosin staining (10 magnification). The Control group showed a normal (Naive) colon without DSS treatment. In the DSS-placebo mice, dense cellular fibrosis was observed in the colonic submucosa with regenerative changes. In AT1aR-A treated mice, the colon showed almost normal mucosa architecture and mild edemas in the submucosa. B) Representative histologic sections of distal colon are shown after undergoing TUNEL staining (20 magnification) of the colon. Note the prominent apoptosis in DSS-placebo mice as represented by a dense brown staining. Whereas only mild apoptosis is noted in AT1aR-A treated mice. (representative positive (brown) cells denoted with arrow heads) C) Histologic evaluation of each study group. Note that the histologic score, severity of inflammation, was performed using standard Hematoxylin and Eosin staining. D) Apoptosis index was quantified by dividing total stained apoptosis cells by whole epithelial cell numbers.
Figure 11:
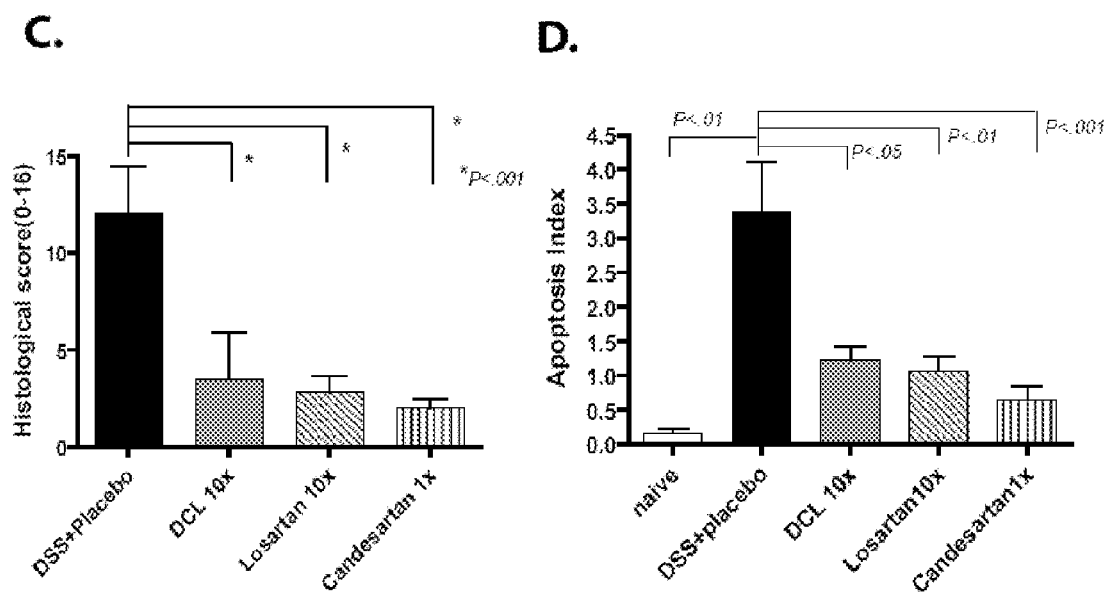
Figure 12:
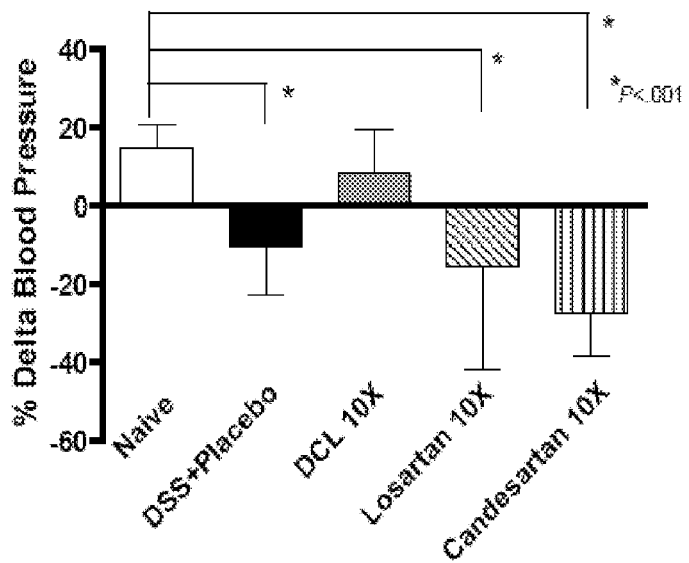
FIG. 12 shows blood pressure (BP) and Heart rate (HR): To test the systemic effect of each compound blood pressure (Delta: Systolic BP and HR after drug infusion–Systolic BP and HR before infusion) was determined. Losartan and Candesartan resulted in a decline, but DCL did not significantly change in BP and blood flow.
Figure 12:
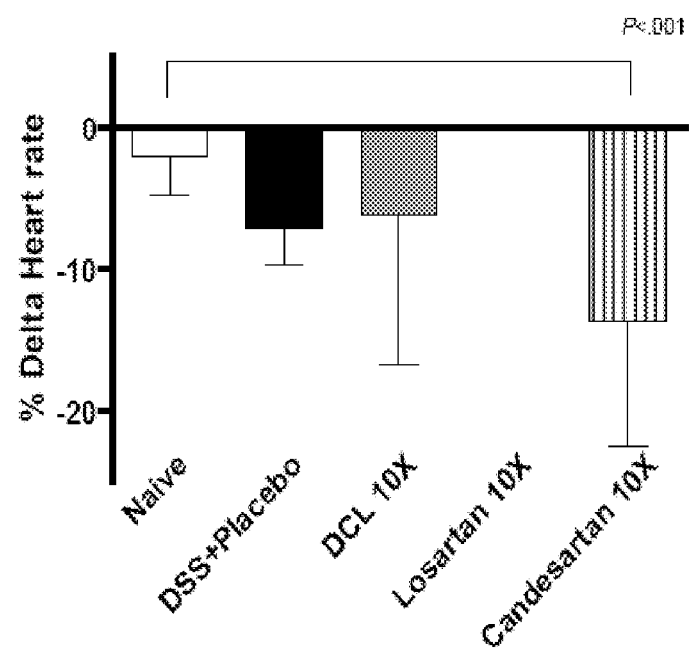
Figure 13:
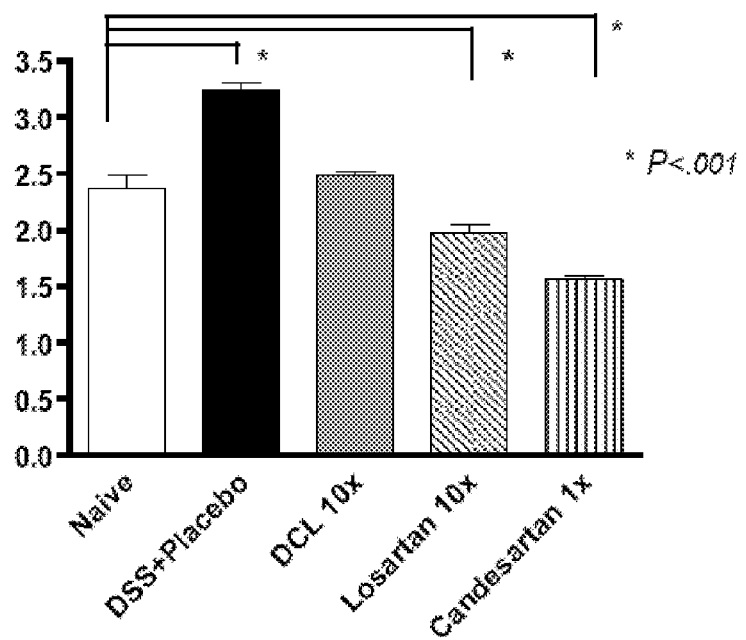
FIG. 13 shows mesenteric and mucosal distal colon blood flow measured by laser Doppler perfusion imager. Losartan and Candesartan resulted in a decline, but DCL did not significantly change. The scores were compared to the Naïve cohort.
Figure 13:
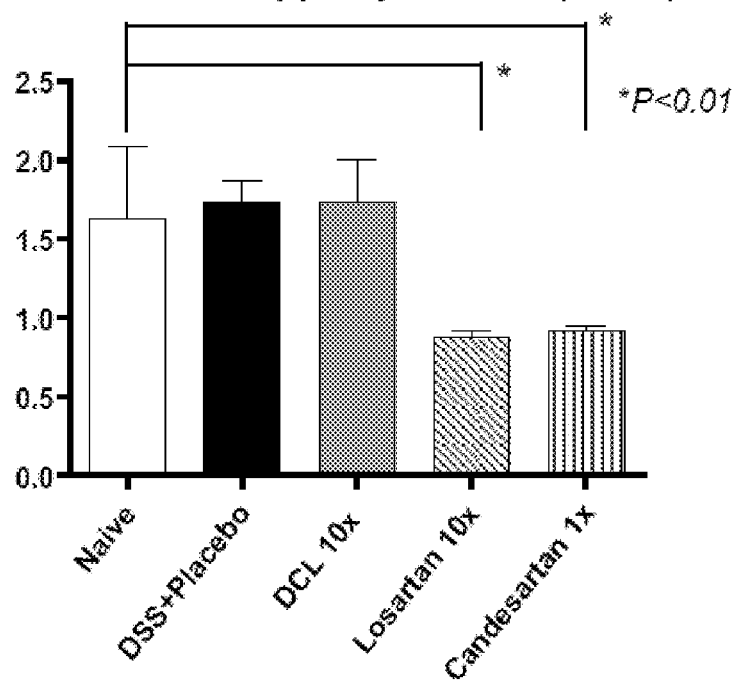

Thus, co-administration of a compound comprising an AT1a antagonist/inhibitor or derivative thereof with another therapeutic (e.g., steroid and/or ACE inhibitor) has the advantage of less systemic immunosuppressive action on the patient (for example, due to the ability of administering lower doses of a steroid in combination with compositions and methods of the present invention (e.g., compared to the level of steroid required to provide the same effect in the absence of a composition of the present invention)); as well as the ability to give higher doses of the AT1a antagonist/inhibitor or derivative thereof without systemic influence (See, e.g., FIGS. 11-13).

TNF-α is known to be markedly up-regulated in inflammatory bowel disease conditions (e.g., including Crohn's disease and ulcerative colitis). Second, TNF-α alters growth and survival characteristics of colonic mucosal epithelial cells. A major mechanism in colitic conditions is an increase in epithelial cell death (apoptosis). Thus, although an understanding of the mechanism is not necessary to practice the present invention and the present invention is not limited to any particular mechanism of action, administration of a compound comprising an AT1a antagonist/inhibitor or derivative thereof markedly decreases the rate of epithelial cell apoptosis and/or increases the rate of epithelial cell proliferation. A combined effect of these actions on the mucosal surface is to allow for healing of the injured colonic lining (e.g., improving the histologic appearance during a colitic episode).

The present invention also provides the ability to coat the gastrointestinal mucosal lining. Use of a composition comprising polyethylene glycol (e.g., PEG with a molecular weight of around 1000 to around 1500) and an AT1a antagonist/inhibitor or derivative thereof provides for the delivery of the AT1a antagonist/inhibitor or derivative thereof with a non-irritating, relatively inert, non-toxic agent (e.g., polyethylene glycol). A number of different forms of polyethylene glycol are contemplated to be useful in the present invention including, but not limited to, 200, 300, 400, 600, 1000, 1450, 3350, 4000, 6000, 8000 and 20000 molecular weight polyethylene glycol. In some embodiments, polyethylene glycol of 1000-4000 MW is utilized (e.g., to reduce the absorption of an AT1a antagonist through the GI mucosa). In some embodiments, polyethylene glycol of 1000-1450 MW is utilized. Polyethylene glycol used in the present invention may be linear or branched. Although an understanding of the mechanism is not necessary to practice the present invention and the present invention is not limited to any particular mechanism of action, administration of compositions of the present invention with an enema, because polyethylene glycol has viscous consistency, permits the composition comprising polyethylene glycol and an AT1a antagonist/inhibitor to thoroughly coat the colonic wall (e.g., prevents it from falling away from the wall with peristalsis or gravity). In some embodiments, the longer the composition comprising polyethylene glycol and an AT1a antagonist/inhibitor are in contact with inflamed colonic mucosal tissue, the greater the beneficial effect provided to a subject. In some embodiments, a composition comprising polyethylene glycol and an AT1a antagonist/inhibitor are used for oral administration for coating and action on inflamed tissues of the oral cavity, esophagus, stomach and small intestine.

The present invention provides pharmaceutical compositions that comprise an AT1a antagonist/inhibitor, alone, or in combination with at least one other agent, such as a stabilizing compound, ACE inhibitor or a steroid (e.g., prednisone), and may be administered in any sterile, biocompatible pharmaceutical carrier, including, but not limited to, saline, buffered saline, dextrose, PEG, and water.

The methods of the present invention find use in treating (e.g., prophylacticly or therapeutically) diseases, signs or symptoms of diseases, or altering physiological states. A composition comprising an AT1a antagonist/inhibitor or derivative thereof can be administered to a subject (e.g., a patient) in a pharmaceutically acceptable carrier such as physiological saline or water. Standard methods for intracellular delivery of compounds can be used (e.g., delivery via liposome). Such methods are well known to those of ordinary skill in the art. The formulations of this invention are useful for parenteral administration, such as intravenous, intramuscular, and intraperitoneal. In some embodiments, a composition comprising an AT1a antagonist/inhibitor or derivative thereof is delivered via inhalation (e.g., to address inflammatory or pro-fibrotic processes of the pulmonary system). In some embodiments, a composition comprising an AT1a antagonist/inhibitor or derivative thereof is delivered by intra-articular injection (e.g., into an inflamed or fibrotic joint space). In other embodiments, a composition comprising an AT1a antagonist/inhibitor or derivative thereof is delivered to isolated inflamed areas (e.g., the bladder, cardiac tissue, central nervous system, etc.) via direct injection."

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments of the present invention, compositions and/or formulations comprising an AT1a antagonist/inhibitor or derivative thereof can be administered to a subject alone, or in combination with other drugs, small molecules, or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions comprising an AT1a antagonist/inhibitor or derivative thereof is administered alone to individuals subject to or suffering from a disease or condition (e.g., inflammatory bowel disease).

These pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; enteral administration rectal administration (e.g., transanal administration), as well as parenteral delivery, including intramuscular, subcutaneous, intramedullary, intrathecal, intraventricular, via inhalation, injection into the urinary system, intraperitoneal, or intranasal administration.

For injection (e.g., intra-articular injection (e.g., into an inflamed or fibrotic joint space)), the pharmaceutical compositions of the invention may be formulated in aqueous solutions, preferably in physiologically compatible buffers such as Hanks' solution, Ringer's solution, or physiologically buffered saline.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, e.g., for oral or nasal ingestion, inhalation, or intracardiac injection by/to a patient to be treated.

Pharmaceutical compositions suitable for use in the present invention include compositions wherein the active ingredients are contained in an effective amount to achieve the intended purpose. For example, an effective amount of the pharmaceutical agent may be that amount that reduces inflammation associated with inflammatory bowel disease or that alters the expression of NF-κB and/or TNF-α and/or other pro-inflammatory and pro-fibrotic cytokines. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. Preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

In some embodiments, multiple therapeutic agents (e.g., at least one of which is an angiotensin II receptor Type 1a (AT1a) antagonist or derivative thereof described herein) are co-administered (e.g., are administered in any order or even simultaneously to the same subject). If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to several (e.g., 2, 3, 4 or more) weeks. The therapeutic agents co-administered may be administered via different routes (e.g., a first therapeutic agent (e.g., AT1a antagonist or derivative thereof) is administered orally, and a second therapeutic agent (e.g., ACE-inhibitor) is administered transanally).

In some embodiments, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

Formulations include those suitable for oral, parenteral (e.g., including subcutaneous, intradermal, intramuscular, intravenous, intraarticular, and intramedullary), intraperitoneal, transmucosal, transdermal, rectal and topical (including dermal, buccal, sublingual, ophthalmic, and intraocular) administration although the most suitable route may depend upon for example the condition and disorder of the recipient. The formulations may conveniently be presented in unit dosage form and may be prepared by any of the methods well known in the art of pharmacy. Methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

For oral administration, compositions of the invention can be formulated readily by combining the active compounds (e.g., AT1a antagonists) with pharmaceutically acceptable carriers or excipients well known in the art. Such carriers enable the compounds of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethyl cellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. All formulations for oral administration should be in dosages suitable for such administration.

Thus, for administration, a satisfactory result may be obtained employing an AT1a antagonist/inhibitor or derivative thereof in an amount within the range of from about 0.01 mg/kg to about 10 mg/kg, or more (e.g., 10-20, 20-40, 40-80, 80-100 mg/kg or more), and preferably from about 0.1 mg/kg to about 200 mg/kg, alone or in combination with other drugs, with the other drugs being employed together in the same oral dosage form or in separate dosage forms taken at the same time.

In some embodiments, an oral dosage form, such as tablets or capsules, will contain the AT1a antagonist/inhibitor or derivative thereof in an amount of from about 1 to about 500 mg, preferably from about 125 to about 200 mg, and more preferably from about 25 to about 150 mg.

For parenteral administration, the ACE inhibitor will be employed in an amount within the range of from about 0.001 mg/kg to about 10 mg/kg or more (e.g., 20, 30, 40, 50 or more mg/kg) and preferably from about 0.01 mg/kg to about 1 mg/kg.

In some preferred embodiments, a composition comprising an AT1a antagonist/inhibitor is administered to a subject via a transanal route (e.g., via an enema). The present invention is not limited by the amount or type of AT1a antagonist/inhibitor used for administration via a transanal route (e.g., via an enema). For example, in some embodiments, an enema will contain from about 0.01 mg/kg to about 1000 mg/kg of the AT1a antagonist/inhibitor per kilogram weight of the subject administered the enema, although lower and higher concentrations are contemplated. For example, in some embodiments, an enema will contain between 0.1 and 1 µg of the AT1a antagonist/inhibitor per kilogram weight of the subject administered the enema. In some embodiments, an enema will contain between 1.0 and 10 µg of the AT1a antagonist/inhibitor per kilogram weight of the subject administered the enema. In some embodiments, an enema will contain between 10 and 100 µg of the AT1a antagonist/inhibitor per kilogram weight of the subject administered the enema. In some embodiments, an enema will contain between 100 µg and 1 mg of the AT1a antagonist/inhibitor per kilogram weight of the subject administered the enema. In some embodiments, an enema will contain between 10 µg/kg to 10 mg/kg of the AT1a antagonist/inhibitor per kilogram weight of the subject administered the enema. In some embodiments, an enema will contain between 1 mg and 10 mg of the AT1a antagonist/inhibitor per kilogram weight of the subject administered the enema. In some embodiments, an enema will contain between 10 mg and 100 mg of the AT1a antagonist/inhibitor per kilogram weight of the subject administered the enema. In some embodiments, an enema will contain between 100 mg and 1000 mg of the AT1a antagonist/inhibitor per kilogram weight of the subject administered the enema. In some embodiments, an enema will contain between 1000 mg and 10000 mg of the AT1a antagonist/inhibitor per kilogram weight of the subject administered the enema. In some embodiments, an enema will contain more than 10000 mg of the AT1a antagonist/inhibitor per kilogram weight of the subject administered the enema. In some embodiments, an enema is administered to a subject once daily. In some embodiments, an enema is administered to a subject twice daily. In some embodiments, an enema is administered to a subject three or more times a day. In some embodiments, an enema is administered to a subject one, two, three or more times a week. In some embodiments, the AT1a antagonist/inhibitor administered to a subject via an enema is any one or more of the AT1a antagonist/inhibitor described herein. Thus, in some embodiments, 0.01 mg/kg to 10000 mg/kg of AT1a antagonist/inhibitor per kilogram weight of the subject (e.g., 10 mg/kg to 1000 mg/kg) is given per dose to a subject (e.g., enterally), wherein dosing could be from once to 3 times a day, or more.

The composition described above may be administered in the dosage forms as described above in single or divided doses of one to multiple times daily, or continuously or semi-continuously (See e.g., U.S. Pat. No. 6,267,990 for controlled release techniques, herein incorporated by reference in its entirety).

Compositions comprising a compound of the invention formulated in a pharmaceutical acceptable carrier may be prepared, placed in an appropriate container, and labeled for treatment of an indicated condition. For compositions or formulations comprising AT1a antagonist/inhibitor, conditions indicated on the label may include treatment of condition related to prophylactic or therapeutic treatment of inflammatory bowel disease.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount which ameliorates or prevents signs and/or symptoms of a disease state or condition. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use.

The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject's physician in view of the patient to be treated. Dosage and administration are adjusted to provide sufficient levels of the active moiety or to maintain the desired effect (e.g., reduction of inflammatory colonic tissue). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions of the present invention may be administered in a number of ways depending upon whether local or systemic treatment is desired and upon the area to be treated (e.g., depending upon the treatment target (e.g., inflammatory and/or fibrotic targets)). Administration may be oral, enteral, topical (including ophthalmic and to mucous membranes including vaginal and rectal delivery), pulmonary (e.g., by inhalation or insufflation of powders or aerosols, including by nebulizer; intratracheal, intranasal, epidermal and transdermal), or parenteral. Parenteral administration includes intravenous, intraarterial, subcutaneous, intraperitoneal or intramuscular injection or infusion; or intracranial, e.g., intrathecal or intraventricular, administration. As described above, compositions and formulations comprising AT1a antagonist/inhibitor or derivatives thereof are believed to be particularly useful for enteral administration.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provides pharmaceutical compositions containing (a) an AT1a antagonist/inhibitor or derivative or analogue thereof, and (b) one or more other agents (e.g., an ACE inhibitor, a steroid, etc.). Examples of steroids include, but are not limited to, cortisol, prednisone and other corticosteroids. In some embodiments, two or more combined agents (e.g., steroids) may be used together or sequentially.

The present invention also includes methods involving co-administration of compounds comprising an AT1a antagonist/inhibitor or derivative or analogue thereof described herein with one or more additional active agents (e.g., an ACE inhibitor, a steroid (e.g., a corticosteroid)). Indeed, it is a further aspect of this invention to provide methods for enhancing prior art therapies and/or pharmaceutical compositions by co-administering a composition comprising an AT1a antagonist/inhibitor or derivative or analogue thereof of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered agents may each be administered using different modes or different formulations.

The agent or agents to be co-administered depends on the type of condition being treated. For example, when the condition being treated is an inflammatory bowel disease, the additional agent can be a corticosteroid, or other type of immunosuppressive agent. The additional agents to be co-administered, such as immunosuppressive agents or corticosteroids can be any of the well-known agents in the art, including, but not limited to, those that are currently in clinical use.

In some embodiments, the present invention provides drug screening assays (e.g., to screen for AT1a antagonist derivatives and/or analogs that retain biological activity (e.g., antagonist/inhibitory activity)). In some embodiments, screening methods of the present invention utilize biomarkers (e.g., including but not limited to NF-kB, TNF-a (tumor necrosis factor-alpha); interleukin-1b (IL-1b); IL-6; IL-10; transforming growth factor-beta (TGF-b), Foxp3 (a T-cell regulatory factor), IL-12p40, the regulatory factor for interleukin-12 (IL-12), and a key regulator for the up-regulation of interferon gamma (IFN-g); IFN-g; IL-17, angiotensin II type 1a receptor (AT1aR) and ADAM17 (metallopeptidase domain 17 (ADAM17), also called TACE (tumor necrosis factor-α-converting enzyme)).

For example, in some embodiments, the present invention provides a method of screening for a compound (e.g., test compound or candidate compound (e.g., AT1a antagonist derivative or analogue)) that alters (e.g., increases or decreases) the presence of biomarkers (e.g., NF-kB or downstream target molecules). In some embodiments, candidate compounds are derivatives and/or analogues of a sartan family member (e.g., losartan, candesartan, azilsartan, eprosartan, irbesartan, valsartan, olmesartan, telmisartan or tasosartan). In some embodiments, the candidate compound in a synthetic molecule generated to mimic the biological activity of a sartan or other type of AT1a antagonist. The present invention is not limited by the type of candidate compound utilized. Indeed, a variety of candidate compounds may be tested including, but are not limited to, carbohydrates, monosaccharides, oligosaccharides, polysaccharides, amino acids, peptides, oligopeptides, polypeptides, proteins, nucleosides, nucleotides, oligonucleotides, polynucleotides, including DNA and DNA fragments, RNA and RNA fragments and the like, lipids, retinoids, steroids, drug, antibody, prodrug, glycopeptides, glycoproteins, proteoglycans and the like, and synthetic analogues or derivatives thereof, including peptidomimetics, small molecule organic compounds and the like, and mixtures thereof.

In some embodiments, test compounds are screened (e.g., characterized) for their ability to alter (e.g., reduce) clinical parameters of inflammatory bowel disease and/or signs or symptoms of inflammatory bowel disease. The present invention is not limited by the clinical parameter and/or sign or symptom of inflammatory bowel disease being measured. Indeed a variety of clinical parameters and signs or symptoms of inflammatory bowel disease can be measured including, but not limited to, growth retardation, rectal prolapse, blood in stools (e.g., melena and/or hematochezia), wasting, iron deficiency, and anemia (e.g. iron deficiency anemia and anemia of chronic disease or of chronic inflammation, and weight loss.

In one screening method, test compounds are evaluated for their ability to alter biomarker presence, activity or expression by contacting a test compound with a cell (e.g., a cell expressing or capable of expressing biomarker nucleic acid and/or protein) and then assaying for the effect of the test compounds on the presence or expression of a biomarker. In some embodiments, the effect of candidate compounds on expression or presence of a biomarker is assayed for by detecting the level of biomarker mRNA expressed by the cell. mRNA expression can be detected by any suitable method.

In other embodiments, the effect of test/candidate compounds on expression or presence of biomarkers is assayed by measuring the level of polypeptide encoded by the biomarkers. The level of polypeptide expressed can be measured using any suitable method including, but not limited to, those disclosed herein.

Specifically, the present invention provides screening methods for identifying modulators, i.e., candidate or test compounds or agents (e.g., proteins, peptides, peptidomimetics, peptoids, small molecules or other drugs) that bind to or otherwise directly or indirectly affect biomarkers, have an inhibitory (or stimulatory) effect on, for example, biomarker (e.g., NF-kB or other biomarker described above) expression, biomarker activity or biomarker presence, or have a stimulatory or inhibitory effect on, for example, the expression or activity of a biomarker substrate. Compounds thus identified can be used to modulate the activity of target gene products (e.g., biomarker genes) either directly or indirectly in a therapeutic protocol, to elaborate the biological function of the target gene product, or to identify compounds that disrupt normal target gene interactions. Compounds that inhibit or enhance the activity, expression or presence of biomarkers are useful in the treatment of inflammatory bowel disorders, diseases or the like.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37:2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (See, e.g., Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that expresses or is capable of generating a biomarker is contacted with a test compound, and the ability of the test compound to modulate biomarker presence, expression or activity is determined. Determining the ability of the test compound to modulate biomarker presence, expression or activity can be accomplished by monitoring, for example, changes in enzymatic activity or downstream products of expression (e.g., cellular integration and/or synaptic connectivity).

The ability of the test compound to modulate biomarker binding to a compound (e.g., a biomarker substrate or binding partner) can also be evaluated. This can be accomplished, for example, by coupling the compound (e.g., the substrate or binding partner) with a radioisotope or enzymatic label such that binding of the compound (e.g., the substrate) to a biomarker can be determined by detecting the labeled compound (e.g., substrate) in a complex.

Alternatively, the biomarker can be coupled with a radioisotope or enzymatic label to monitor the ability of a test compound to modulate biomarker binding to a biomarker substrate in a complex. For example, compounds (e.g., substrates) can be labeled with $^{125}$I, $^{35}$S $^{14}$C or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., AT1a antagonist derivative) to retain biological activity (e.g., antagonist/inhibitory activity of the AT1a receptor) with or without the labeling of any of the interactants can be evaluated. For example, a microphysiometer can be used to detect the interaction of a compound with a biomarker without the labeling of either the compound or the biomarker (McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a biomarker.

In yet another embodiment, a cell-free assay is utilized. Cell-free assays involve preparing a reaction mixture of the target gene protein and the test compound under conditions and for a time sufficient to allow the two components to interact and bind, thus forming a complex that can be removed and/or detected.

The interaction between two molecules (e.g., a biomarker protein and a test compound) can also be detected (e.g., using fluorescence energy transfer (FRET) (See, e.g., Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determining biologic activity of a target molecule can be accomplished using real-time Biomolecular Interaction Analysis (BIA) (see, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIA-CORE). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

This invention further pertains to novel agents identified by the above-described screening assays. Accordingly, it is within the scope of this invention to further use an agent (e.g., test compound) identified as described in an appropriate animal model (such as those described herein) to determine the efficacy, toxicity, side effects, or mechanism of action, of treatment with such an agent. Furthermore, novel agents identified by the above-described screening assays can be, for example, used for treatments as described herein.

EXPERIMENTAL

The following examples are provided in order to demonstrate and further illustrate certain preferred embodiments and aspects of the present invention and are not to be construed as limiting the scope thereof.

Example 1

Design and Characterization of AT1a Antagonists

Analogs that are closely related structurally to losartan (See, e.g., compound 1 in FIG. 2) and candesartan (See, e.g., FIG. 3, below) are provided. Each analog has structural attributes that render the molecules highly impermeable to cell membranes (both epithelial cells and adjacent vasculature). This limits the analogs' exposure in vivo to the intestine alone.

AT1a antagonists: Analogs 2, 3 and 4 are based on losartan 1 (See FIG. 2). Losartan analog 2 lacks the chloro group on the imidazole molecule and has hydrogen in its place. Losartan analog 3 lacks the chloro group on the imidazole molecule, and possesses a carboxylic acid instead of the hydroxylmethyl group. These changes are designed to yield very low intestinal absorption. Compound 5, similar to 2, lacks the chloro group on the imidazole molecule, and the hydroxymethyl group has been replaced by a carboxylic acid. Compounds 6 and 7, are similar to compounds 3 and 4, except that carboxylic acids replace the ester groups. The diacidic nature of targets 5-7, in some embodiments, renders these molecules even less absorbable (e.g., orally bioavailable) than monoacidic compounds 2-4.

The present invention also provides compound 8. In this case a highly acidic sulfonic acid has replaced the carboxylic acids of related compounds 3 and 4. Thus, in some embodiments, the present invention provides analogs and/or derivatives of losartan (e.g., designed to decrease its absorption) wherein the hydroxymethyl group is replaced with one or more charged moieties (e.g., an acidic moiety (e.g., carboxylic acid, sulfonic acid and/or other moiety)). In some embodiments, the present invention provides analogs and/or derivatives of losartan (e.g., designed to decrease its absorption) wherein the hydroxymethyl group is replaced with one or more moieties that increases its polarity and/or increases its negative charge. In some embodiments, an analogue or derivative has two acidic functionalities, three acidic functionalities, four or more acidic functionalities (e.g., 5, 6, 7, 8 or more).

Figure 4:
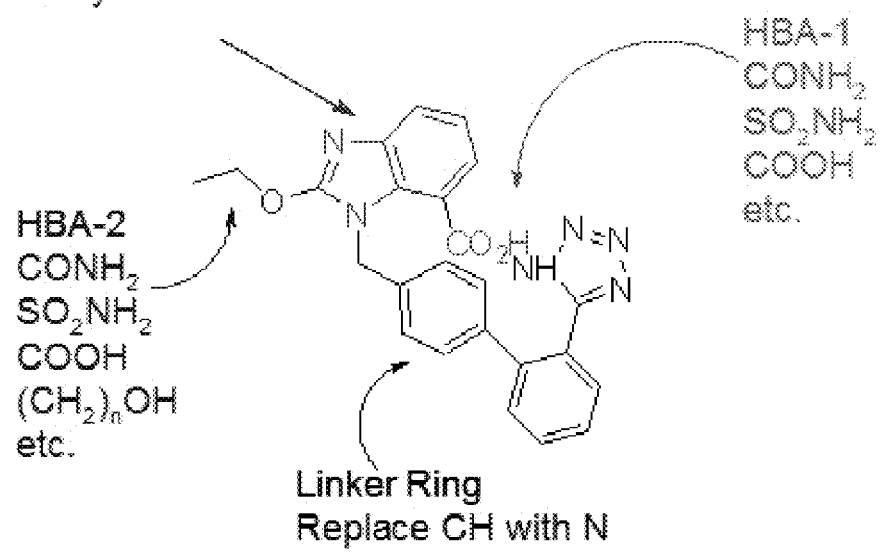
FIG. 4 shows candesartan and several examples of synthesis schemes for generating derivatives/analogs thereof.

In some embodiments, the present invention provides analogs and/or derivatives of candesartan designed to match or exceed the postulated interactions of candesartan with key residues of the AT1a receptor. For example, in some embodiments, two hydrogen bond acceptor (HBA1 and HBA2)) functionalities are strategically positioned on a bicyclic heterocycle (HC) scaffold (See FIG. 4). In some embodiments, conversion of selected aromatic C—H moieties to N are also made (See FIG. 4).

Example 2

Synthetic Strategy

Figure 5:
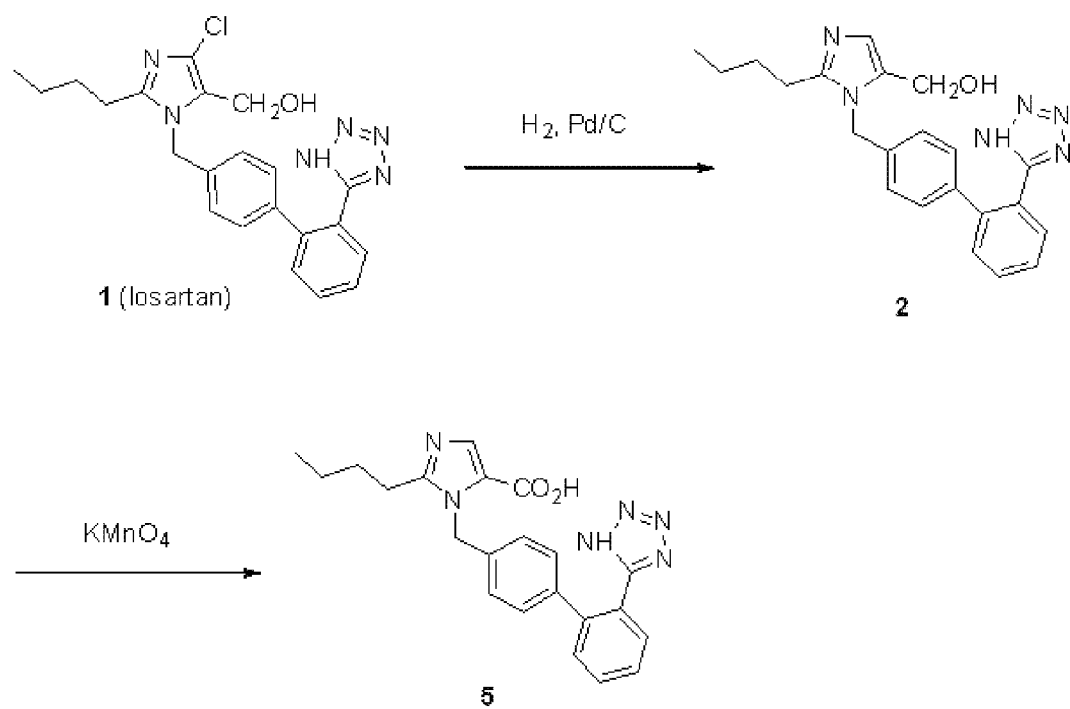
FIG. 5 shows synthesis schemes for making derivatives/analogs.
Figure 6:
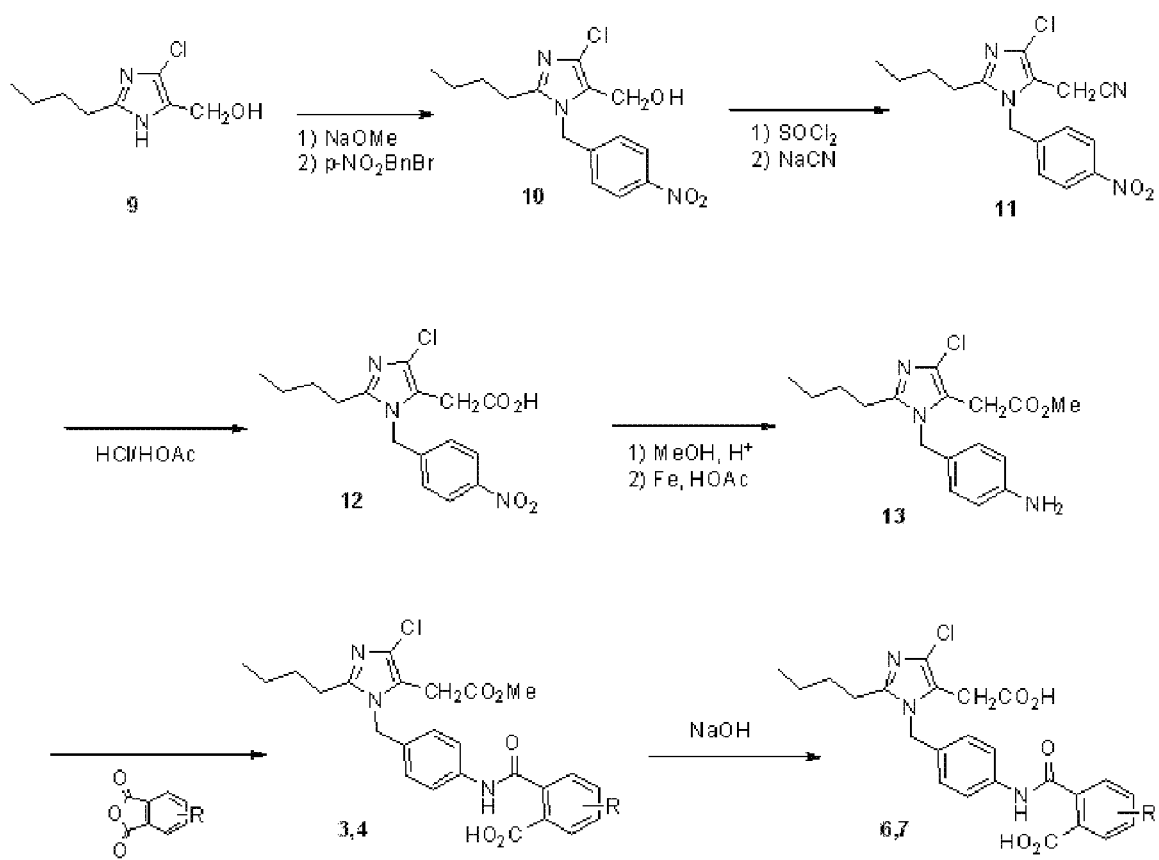
FIG. 6 shows synthesis schemes for making derivatives/analogs.
Figure 7:
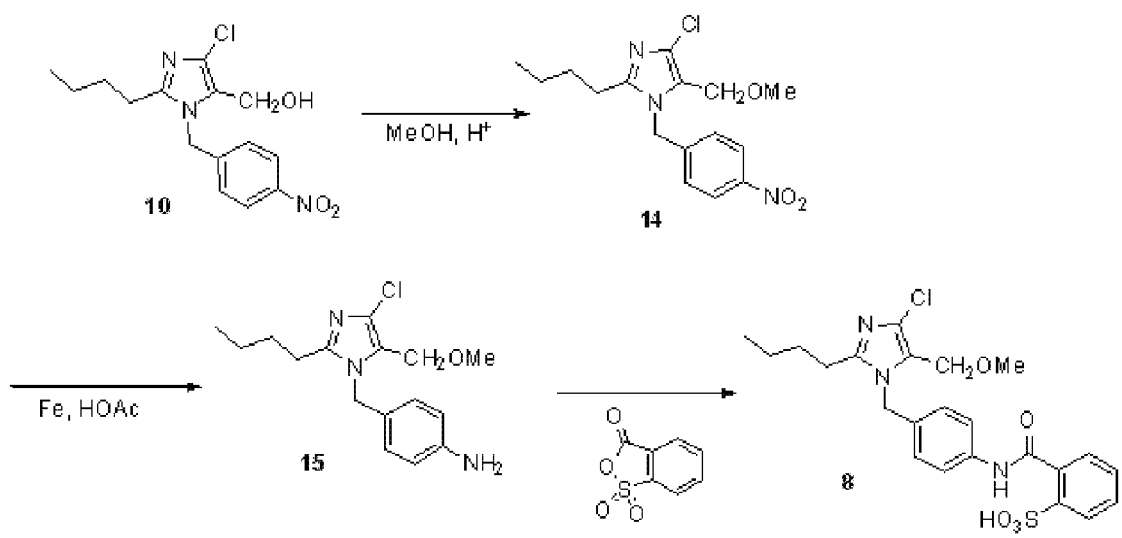
FIG. 7 shows synthesis schemes for making derivatives/analogs.

A variety of synthetic routes utilized to generate analogs and/or derivatives are shown in FIGS. 5-7. For example synthesis schemes for losartan analogs and/or derivatives are shown in FIG. 5. The losartan analogue 2 is prepared from readily available losartan 1 in a single step by catalytic hydrogenolysis of the chloro group (See FIG. 5). In some embodiments, the analog 2 is readily oxidized to the novel carboxylic acid 5 with a manganese-based oxidizing agent. Compounds 3 and 4 (Shown in FIG. 6) are prepared starting with commercially available 2-butyl-4-hydroxymethyl-5-chloroimidazole 9. Diacids 6 and 7 are then obtained by simple saponification of the corresponding esters 4 and 3, respectively. Compound 8 is prepared by the route shown in FIG. 7, starting with compound 10 prepared in FIG. 4. The present invention can utilize a number of analytical methods (e.g., including, but not limited to, NMR, MS, HPLC and combustion analyses) to characterize the purity and/or identity of derivatives and/or analogs.

Example 3

Screening and Characterization of AT1a Antagonists

Materials and Methods

Animals. Specific pathogen-free male, 8-week old C57BL/6 mice (Taconic Farms Inc, Germantown, N.Y.) were maintained in a 12-h night rhythm at 23° C. and a relative humidity of 40-60%. Animals were fed standard rodent chow (LabDiet 5001Rodent Diet, PMI Nutrition International, LLC, Brentwood, Mo.) ad libitum. All experiments were approved by the University Committee on Use and Care of Animals at the University of Michigan.

In vitro assessment of AT1aR antagonism. The present invention provides high throughput screening methods to detect AT1a antagonism in an in vitro setting. A variation of an in vitro model established by McAllister-Lucas et al. (See, e.g., McAllister-Lucas et al., PNAS, 2007; 104:139-44) was used to measure the degree of antagonism on AT1a receptor signaling. This model makes use of the fact that Ang II-dependent stimulation of the AT1a receptor results in rapid activation of the NF-κB transcription factor. In this model, HepG2-AR cells, which stably express the AT1a receptor, were transiently transfected with an NF-κB-luciferase reporter plasmid and a control renilla plasmid (to correct for transfection efficiency). Cells were then treated with or without Ang II (1 μM) for 16 hours in the presence or absence of varying doses of either losartan or deschlorolosartan. Cells were harvested and the luciferase/renilla ratio determined using the Promega Dual Luciferase Assay Kit. Cells were treated (in triplicate) with either media alone (negative control), Ang II (1 μM), Ang II plus losartan (0.1-100 μM), or Ang II plus deschlorolosartan (4-log range of concentration). Loss of Ang II-dependent luciferase induction (measured by luminometer; LMax; Molecular Devices), due to the presence of receptor blockade was then calculated and used to indicate the extent of successful blockade of the AT1a receptor signaling pathway.

Experimental colitis design. Dextran sodium sulfate (DSS) was administered through drinking water for 7 days. Mice were randomly divided into 5 groups. In the DSS+placebo group, mice were given transanal water (total volume 0.25 ml) each day as a control. Three DSS+AT1aR antagonists (AT1aR-A) groups were studied, one containing losartan, one containing DCL, and one containing candesartan suspended in ddH$_2$O at a total volume of 0.25 ml. AT1aR-A were given at 10-fold higher doses (losartan and candesartan: 10 mg/kg/day, candesartan: 1 mg/kg/day) than typically given systemically, and daily dosing was continued for 7 days. The study drugs were administered using a blunt needle via the transanal route. Testing conducted during development of embodiments of the invention characterized that this amount of drug evenly coated the entire colon. A separate group of mice contained naive mice as an additional control group which received plain drinking water ad libitum, and received only water (0.25 ml, transanal) without AT 1 aR-A.

Harvesting. Mice were euthanized 7 days after DSS by carbon dioxide asphyxiation. A 0.5 cm segment taken from the distal half of the colon was excised and placed into 10% formaldehyde. Formalin preserved sections of distal colon were preserved in paraffin, sectioned transversely (5 µm) and stained with hematoxylin and eosin (H&E). The remaining colon was immediately processed for mucosal cell isolation.

Assessment of colitis. The body weight of each mouse, stool characteristics, and intestinal bleeding were recorded. All animals were evaluated daily. Occult bleeding was tested using a hemoccult-card test (Beckman Coulter Inc, Fullerton, Calif.). Histologic grading of colitis was performed in a masked fashion (investigator blinded to the study group) according to previously described methods. (See, e.g., Spencer et al., et al. Dig Dis Sci 2007; 52:1060-70). Crypt shortening and distortion, together with inflammatory infiltrative thickening of the lamina propria, were assigned a score 0 (normal) through 4 (complete loss of crypt, ulceration, and severe thickening of lamina propria). The individual colitis score (0-4) from four quadrants of a left-sided colonic section were summed, such that the maximum score for a given section was 16, and the minimum score was 0. The mean of at least 2 sections were assessed in this manner for each mouse.

Epithelial cell apoptosis assays. A terminal deoxynucleotidyl transferase biotin-dUTP nick end labeling (TUNEL) staining method was used to detect apoptosis, according to manufacturer's instructions (APOPTAG PLUS Peroxidase InSitu Apoptosis Detection Kit, Chemicon International Inc, Temecula, Calif.), with slight modification. Slides were incubated with only one-third of the recommended concentration of TdT enzyme, in order to avoid over-staining. Assessment of apoptosis consisted of separate counting of all TUNEL positive EC in all well oriented crypts and villi separately, and dividing the total number of counted apoptotic cells per number of analyzed crypts and villi, respectively. Apoptotic Index in the region of villi is expressed as the number of TUNEL positive cells per one villus. The addition of both crypt and villus apoptotic indices is expressed as the apoptotic index per crypt-villus complex (at 20× magnification).

Measurements of Blood Pressure and Heart Rate. Blood pressure and heart rate were measured using a noninvasive computerized tail-cuff system (IITC Life Science Inc., Woodland Hills, Calif.) at 1 hour before transanal treatment (Pre) and 2 hr later after treatment (Post) at the day 6 after DSS received. The system was designed to perform all functions automatically, including a programmable routine of cuff inflation and deflation, analysis and assignment of pulse rate and blood pressure, and recording of data electronically. To avoid variations in blood pressures, results were expressed using % Delta Blood Pressure (percent change in systolic pressures prior to and after treatment). Heart rate was also expressed as the change in rate before and after final dosing of transanal drug/placebo.

Mucosal cell isolation and purification. Isolation of mucosal cells was performed using a previously described protocol (See, e.g., Yang et al., J Immunol 2004; 172:4151-8). In brief, colonic tissue, not including the cecum, was placed in RPMI cell culture medium on ice, and fecal contents were gently flushed out. Colonic epithelium was isolated for RNA via opening the colon longitudinally and rinsing with fresh cold RPMI, then the colonic mucosa was mechanically scraped off on a glass slide, and epithelial cells (EC) collected in fresh RPMI with glutamine. These EC were then immediately snap-frozen in liquid nitrogen and processed for RNA extraction.

Real time polymerase chain reaction (RT-PCR). Muscosal scrapings were placed in TRIZOL (Invitrogen), homogenized, RNA extracted and purified as described (See, e.g., Spencer et al., et al. Dig Dis Sci 2007; 52:1060-70). All primers for selected gene sequences were designed using proprietary software (Lasergene, DNA star Inc, Madison, Wis.), and sequences of specific primers are described in Table 1. Real-time PCR(RT-PCR) was performed using a ROTOR-GENE 6000 (Corbett Life Science, Sydney, Australia) and β-actin was used as an internal control for normalization. Fold changes of target genes were calculated using comparative quantification to β-actin.

Stastiscal analysis. Data are reported as mean±standard deviation (SD). Results were analyzed using the t-test for comparison of two means, and a one-way analysis of variance (ANOVA) for comparison of multiple groups. A post-hoc Bonferroni test was used to assess statistical difference between groups. The chi square test was used for categorical data (Prism software; GraphPad Software, Inc., San Diego, Calif.). A value of $P<0.05$ was considered to be statistically significant.

Alternatively, a human renal epithelial cell line (HEK 293) with stable integration of an NF-κB sensitive luciferase reporter vector (NF-κB-PGL4-luciferase; Promega Corp.) is stably infected with retrovirus expressing the AT1a receptor (AT1a-pRET6-EGFP). Cells with high-level integration of retrovirus are isolated by flow-cytometric sorting using EGFP as a marker. Infected cells are used to seed 96-well microtiter plates for AT1a antagonist (e.g., sartane (e.g., sartane derivative/analog)) screening. Each test compound—derivative/analog—is assessed for AT1a receptor blockade: Cells are treated with either media alone (negative control), Ang II (1 µM), Ang II plus losartan (0.1-100 µM), or Ang II plus test compound (e.g., sartane derivative and/or analog)) over a 4-log range of concentration. Following 3-6 hrs of treatment, cells are lysed directly in the wells using Passive Lysis Buffer (Promega), and luciferase levels, reflecting NF-κB activation, are measured using a 96-well luminometer (LMax; Molecular Devices). Loss of Ang II-dependent luciferase induction, due to the presence of inhibitors, is calculated to indicate the extent of blockade of the AT1a receptor signaling pathway.

All test compounds are tested in multiple sets on each 96-well, and values expressed as the mean for each dosing scheme. Antagonism is evaluated using the percent reduction in luciferase activity. Successful AT1a receptor blockade can be defined in a number of ways. In one embodiment, successful receptor blockade is defined as matching (e.g., within about 10% margin) and/or exceeding the percent blockade of NF-κB induction of losartan (e.g., at a concentration of 50 µm). In some embodiments, successful test compounds are utilized for in vivo testing.

For example, des-chloro losartan (compound 2 shown in FIG. 2) was synthesized and tested using this method. The efficacy of losartan vs. des-chloro losartan in blocking Ang II-dependent NF-κB induction was characterized using HepG2 cells stably transfected with the AT1a receptor that transiently expressed the NF-κB luciferase reporter vector.

HepG2-AR cells, which stably express the AT1a receptor, were transiently transfected with an NF-κB-luciferase reporter plasmid and a control renilla plasmid (to correct for transfection efficiency). Cells were then treated with or without Ang II (1 µM) for 16 hours, in the presence or absence of varying doses of either losartan or deschloro losartan (Compound 2). Cells were harvested and the luciferase/renilla ratio determined using a luciferase assay kit (e.g., Promega Dual Luciferase Assay Kit). The average maximal NF-κB induction seen with Ang II alone was 5.95-fold, and this value was set as 100% induction. The fold induction in the presence of varying doses of inhibitor was then converted to a percentage of this maximal induction.

Example 4

In Vitro Assessment of AT1aR Antagonists

Figure 8:
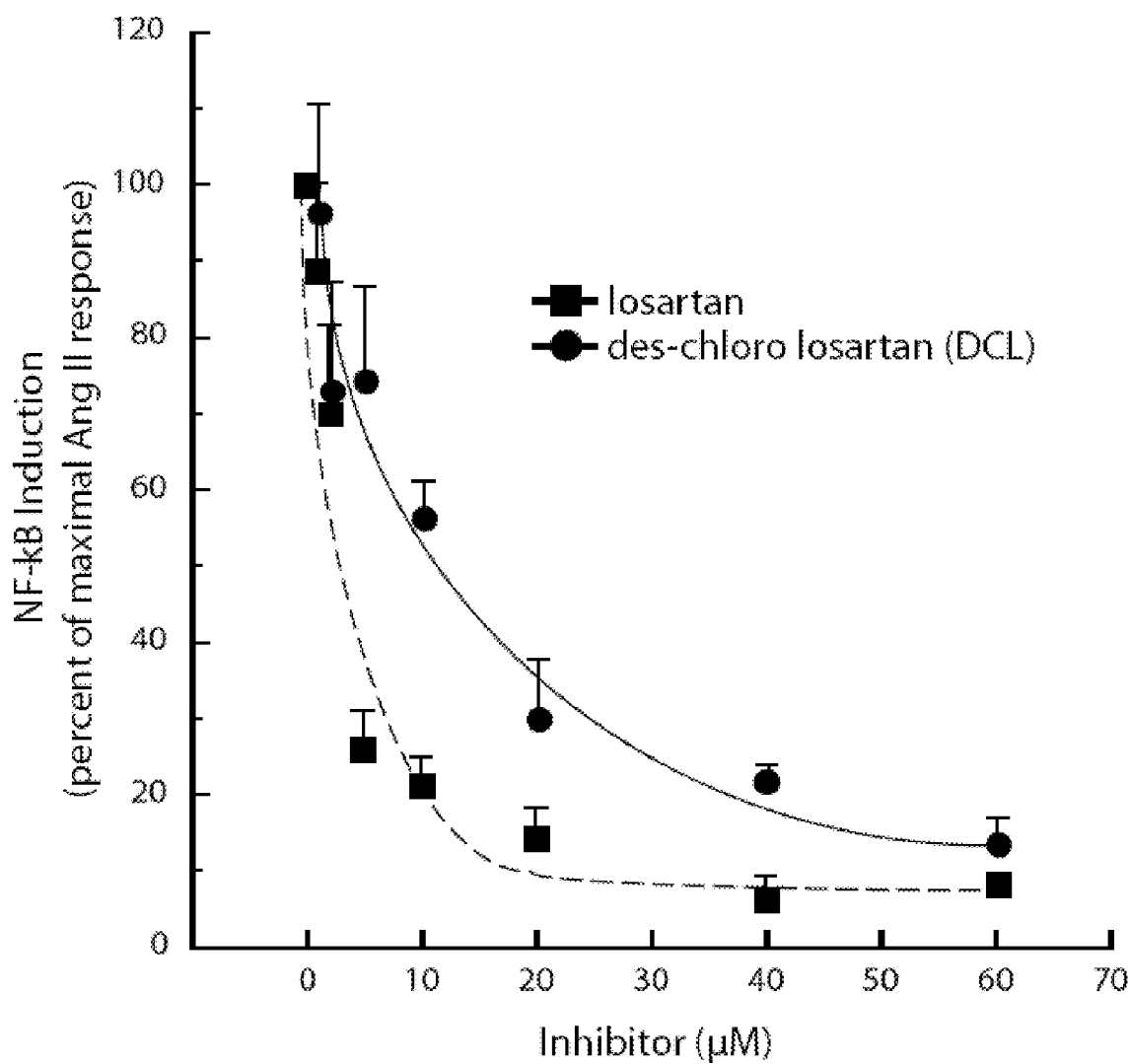

To determine if the losartan analogue (des-chloro losartan, DCL, also referred to as compound 2), had similar antagonism to AT1aR compared to losartan, in vitro assessment was determined by the ability of each compound to prevent NF-κB activation in vitro. FIG. 8 shows the extent of both compound's ability to block NF-κB activation. The average maximal NF-κB induction seen with incubation with angiotensin II alone was 5.95-fold, and this value was set to a level of 100% induction. DCL demonstrated near equal AT1aR antagonism compared to losartan (85% vs. 90% inhibition of NF-κB activation at 60 µM dosing, respectively). Thus, in some embodiments, the present invention provides that DCL significantly inhibits ANG II signaling via AT1a (See FIG. 8). Thus, in some embodiments, the present invention provides AT1aR antagonist analogues that inhibit ANGII signaling via AT1a, and compositions and methods of identifying (e.g., screening for) and characterizing the same (e.g., in vitro, ex vivo and in vivo methods (See, e.g., Examples 3 and 5).

Figure 9:
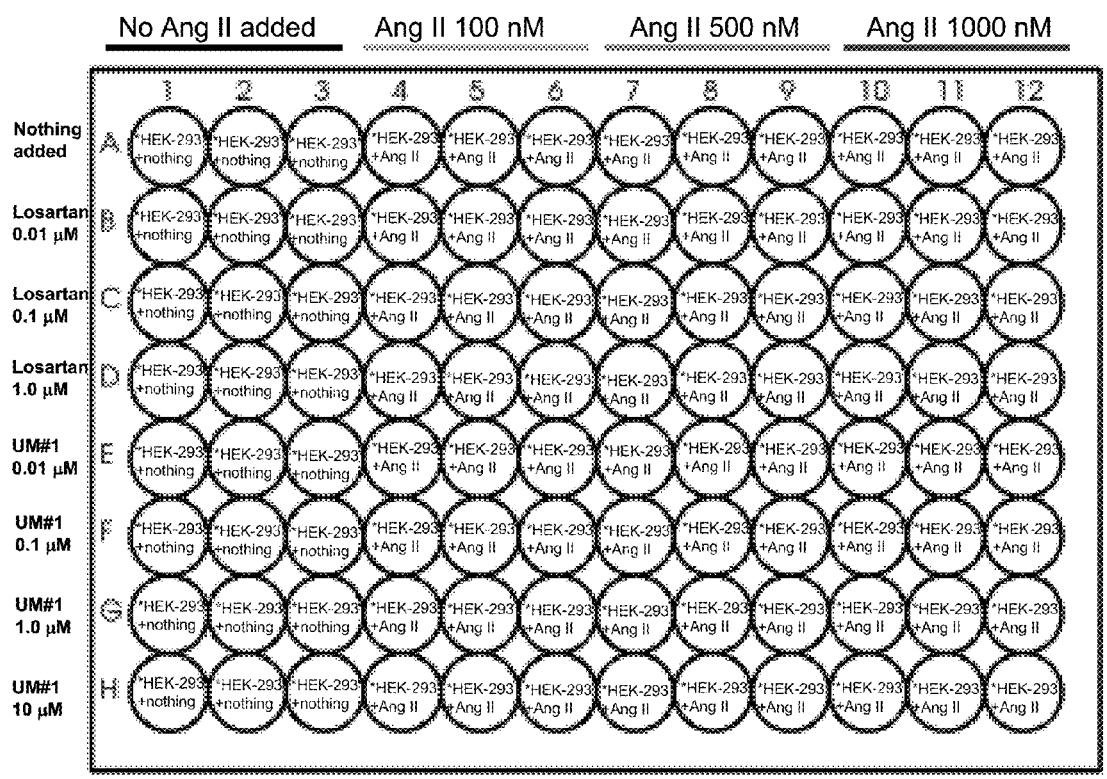
FIG. 9 shows a 96 well assay utilized to screen test compounds.

In addition, screening of test compounds can be configured as shown in FIG. 9 that provides a 96-well set up for the screening of each test compound (e.g., AT1a antagonist). AT1a transfected cells with luciferase reporter are stimulated with varying doses of Ang II, with or without prior blockade with losartan or candidate compound. Dosing of losartan and test compounds (labeled as an example as UM#1) ranges from the "Nothing" added to a 100 µM concentration. Two or more plates can be used to cover the dosing range. Cells are denoted as *HEK-293*, as they are modified HEK-293 cells post-stable transfection with the NF-κB sensitive luciferase reporter vector.

Example 5

Effect of AT1aR Antagonists on Clinical Parameters

After DSS administration, mice developed colitis, which was manifested by loose stools, intestinal bleeding, and weight loss (See Example 3 for methodology).

Figure 10:
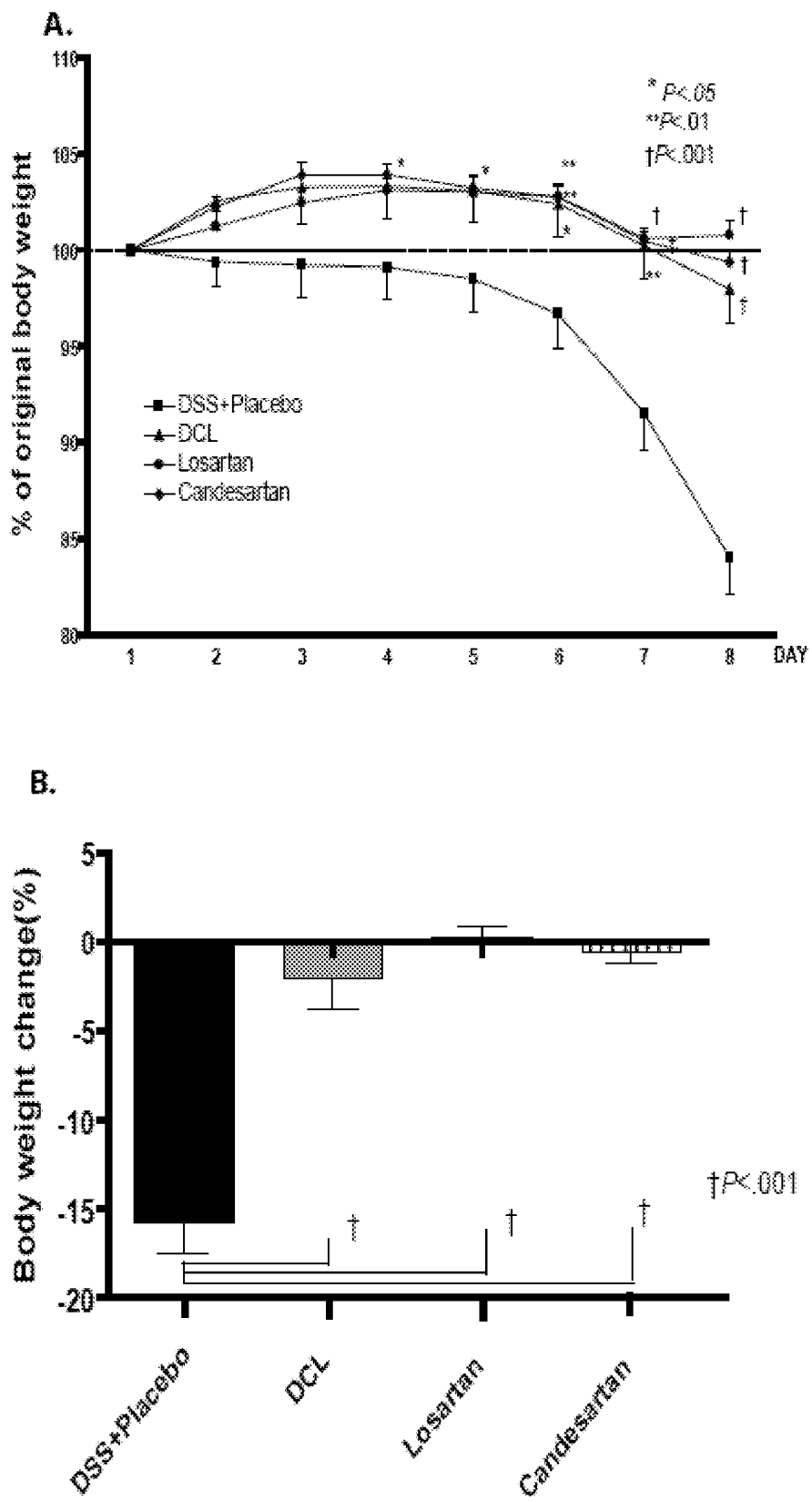
FIG. 10 shows A) Time course of changes in body weight loss. All mice received 2.5% DSS in drinking water. DSS was administrated during the 7 days. All mice were evaluated daily for weight loss, stool consistency, and occult or gross intestinal bleeding. The groups were: DSS-Placebo mice, deschloro-losartan 10× (2,500 µg per dose) treated, Losartan 10× (2,500 µg per dose) treated mice, and Candesartan 1× (250 µg per dose) treated mice. Results are expressed as mean±SD (*P<0.05; **P<0.01; †P<0.001, measurements were compared with placebo for significance.) B) After 7 days, weight loss was severe in the placebo group (−15.81±6.59% weight loss); however, this loss was significantly attenuated in the angiotensin II type Ia receptor antagonists treated (DCL; −2.02±4.34%, Losartan; 0.07±2.50%, Candesartan; −0.63±1.63%: P<0.001, respectively) C) Days to heme positive stool was compared with placebo for significance.

Body weights. Body weight change (reported as percentage change from baseline body weight on day 1) is shown in FIGS. 10A and 10B. As observed in the field (See, e.g., Koga et al., Surgery 2008; 144:259-68), significant weight loss occurs toward the end of 1 week of DSS administration. However, as shown in FIGS. 10A and 10B, administration of an AT1aR antagonist (AT1aR-A) significantly protected against this weight loss (See FIG. 10A, 10B). The difference between the placebo and the AT1aR-A-treated groups became significant after day 5 of DSS. After 1 week, weight loss was severe in the placebo group (15.8±6.5% weight loss); however, this was significantly attenuated in all AT1aR-A groups (DCL: 2.02±4.34%, losartan: 0.07±2.50%, candesartan: 0.63±1.63%; P<0.001 versus placebo; P>0.050 between AT1aR-A groups, respectively).

Figure 10C:
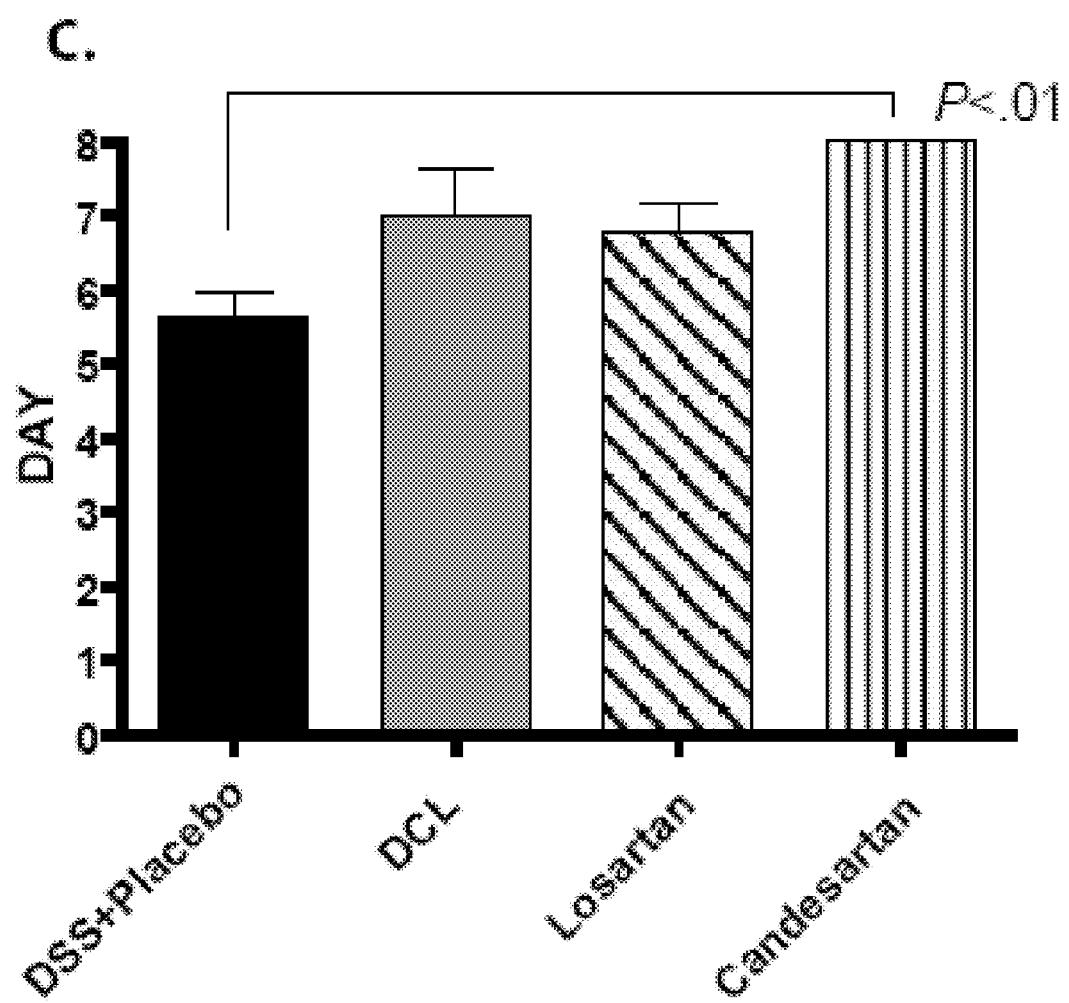

Fecal blood. The onset of heme-positive stools corresponded closely to the development of weight loss (See FIG. 10C). Mice in AT1aR-A groups experienced longer periods before developing heme positive stools (DCL: 7.00±1.4 days, N.S, losartan: 6.8±2.7 days, N.S, candesartan: 8.0±0.0 days, P<0.01) compared to mice in the placebo group (5.64±1.22 days).

Effect of AT1aR-A on histopathology. To evaluate if transanal treatment with AT1aR-A was associated with a reduction in the severity of colitis a blinded histological score at day 8 was assessed. In mice receiving 2.5% DSS, the most severe ulcerative lesions were consistently found in the distal colon, consistent with previous studies (See, e.g., Spencer et al., et al. Dig Dis Sci 2007; 52:1060-70). Severe ulcerative lesions rapidly developed by day 8 of DSS in the placebo group, and these changes were significantly attenuated in the AT1aR-A treated mice (histopathology in FIG. 11A, histologic scores reported in FIG. 11C). The colon of AT1aR-A treated mice showed nearly normal mucosal architecture.

Effect of AT1aR-A on epithelial cell apoptosis. Epithelial cell apoptosis occurred early in the DSS model, as detected by TUNEL positive cells (See FIGS. 11B and 11D). Apoptosis was maximal at day 3 in placebo-treated mice receiving DSS, and apoptotic rates could not be accurately measured at the final time point in the placebo group due to complete loss of epithelial structures. However, large numbers of apoptotic cells were seen in the lumen at day 7, therefore we used the final time point tissues. Enterocyte apoptosis rates were significantly higher in the DSS+placebo group compared to AT1aR-A treatment group. Administration of an AT1aR-A resulted in a significant decline in EC apoptosis rates in DSS colitis. (representative TUNEL staining in FIG. 11B, apoptosis rates reported in FIG. 11D).

Measurements of Blood Pressure and Heart Rate. To test the systemic effect of each compound, blood pressure (Delta BP (post systolic−pre systolic) was determined. Losartan and candesartan resulted in a decline in systolic BP (as shown by a large delta BP in the negative direction); however, DCL did not significantly change BP (See FIG. 12A). Heart rates were not significantly different between the placebo, naïve, DCL, nor losartan groups; however, heart rate declined significantly in the candesartan group compared to the naïve group (See FIG. 12B).

Colonic mucosal and mesenteric blood flow measurements. Mesenteric blood flow measurements showed significantly lower levels in losartan and candesartan treated groups compared to the naïve group (1.97±0.58, 1.56±0.33 vs. 2.82±0.23, P<0.001). On the other hand, in the placebo group (no treatment group), blood flow was significantly elevated compared to naïve mice (3.24±0.30 vs. 2.82±0.23, P<0.001), which identifies a greater inflammatory response (See FIG. 13A). Further, laser Doppler measurements of colonic blood flow at the mucosal level showed a significant decrease for losartan- and candesartan-treated groups compared to naïve (0.88±0.32, 0.92±0.20 vs. 1.91±0.26, P<0.001; FIG. 13B). Interestingly, treatment of mice with DCL failed to change either mucosal or mesenteric blood flow, supporting a lack of systemic or even local-region vascular dilation, which would be associated with AT1aR-A action.

Figure 14:
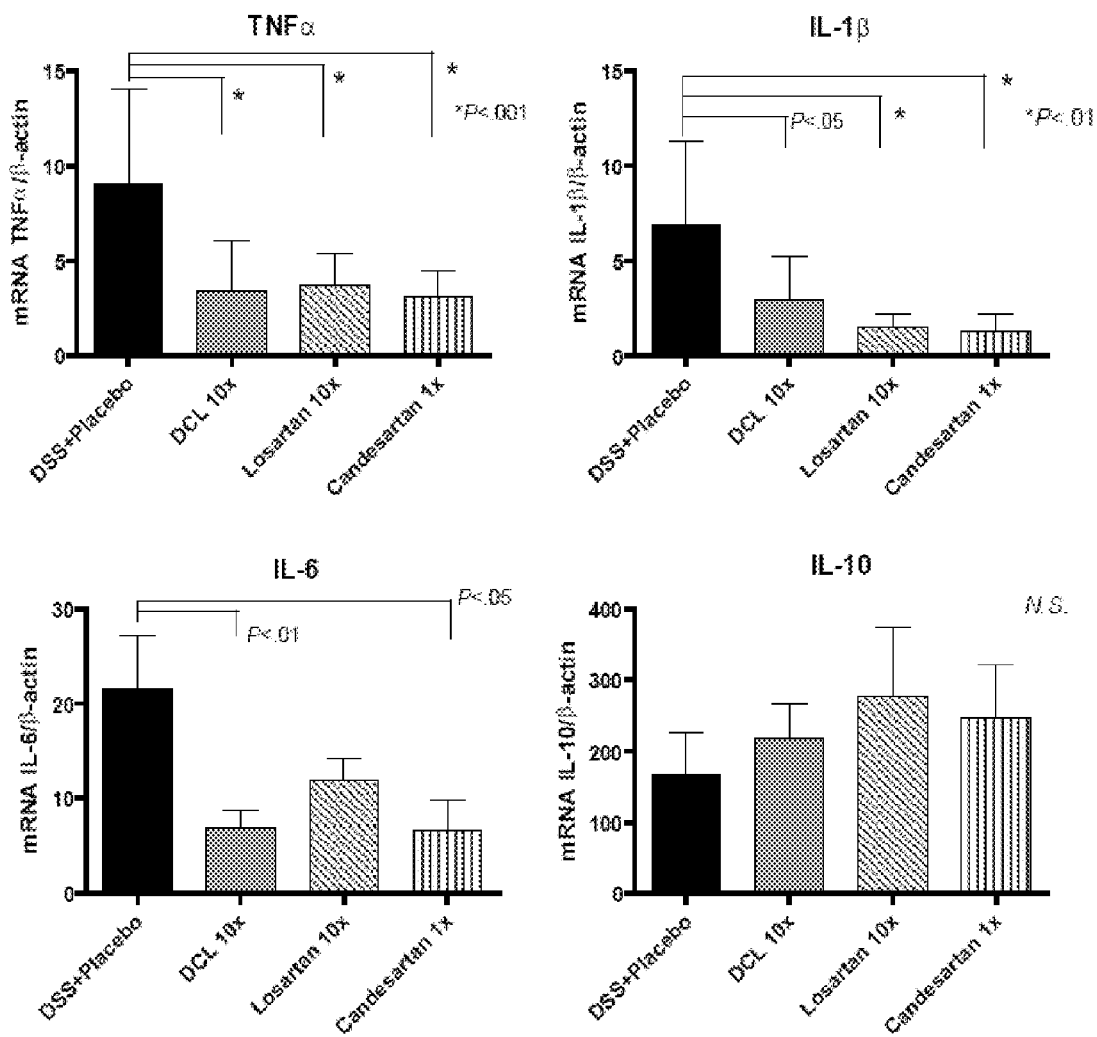
FIG. 14 shows expression of mucosal pro-inflammatory cytokines TNF-α, IL-1β, IL-6, and IL-10 as detected by real time PCR. The mRNA values are expressed relative to β-actin. Error bars indicate mean±SD. Comparisons made using ANOVA with post hoc Bonferroni test.

Effect of AT1aR-A on pro-Inflammatory cytokine expression. TNF-α, IL-1β and IL-6 are pro-inflammatory cytokines that have displayed reduced expression with ACE-I treatment (See, e.g., Spencer et al., et al. Dig Dis Sci 2007; 52:1060-70). Further, these cytokines are known to be up-regulated in the DSS colitis model, and may be responsible for acute tissue injury formation. Therefore, these were quantified as independent biochemical markers of inflammation. FIG. 14 shows mRNA expression of TNF-α, IL-1β and IL-6 as compared to placebo-treated DSS mice. DSS-placebo mice showed significantly increased levels of TNF-α, IL-1β and IL6 mRNA. However, each high dose AT1aR-A compound significantly decreased the mRNA abundance of these cytokines. Furthermore, IL-10 downregulates or completely inhibits expression of several pro-inflammatory cytokines. There was a trend toward higher suppression of inflammatory responses on day 7 in AT1aR-A treatment group in comparison to the placebo group (See FIG. 14).

Accordingly, in some embodiments, the present invention provides compositions and methods for control of colitis (e.g., via transanal administration with each of the AT1a antagonists) as shown by the prevention of apoptosis and weight loss, delay in days to development of blood in the feces, absence of blood pressure and heart rate changes and marked decline in histology. Moreover, compounds designed to have markedly low enteral absorption (e.g., DCL, Compound 2) of the invention were associated with no change in systolic blood pressure, nor changes in colonic blood flow. In sharp contrast, losartan and candasartan, both at dosings comparable to that of DCL, resulted in a significant decline in blood pressure and loss of colonic blood flow. Thus, the present invention provides therapeutic compositions comprising a poorly cell permeable (e.g., that displays poor systemic absorption) AT1a antagonist (e.g., for use in enteral delivery to a subject (e.g., a subject suffering from inflammatory bowel disease)), wherein the compositions effectively treat inflammatory conditions of the intestine (e.g., at a range of dosages (e.g., low to high as described herein)) while concurrently displaying no detectable side-effects (e.g., decline of blood pressure and/or loss of colonic blood flow).

Thus, in some embodiments, the present invention provides that an AT1a receptor antagonist can be utilized with efficacy in treating an inflammatory condition of the intestine when given via the enteral route.

Example 6

Oral Administration of AT1a Antagonists and Derivatives Thereof

Experiments were conducted during development of embodiments of the invention in order to determine if AT1a antagonists or derivatives thereof could treat signs and symptoms of inflammatory bowel disease (e.g., inflammatory conditions of the intestine) when administered orally. Materials and methods were used as described in Example 3 with the following exceptions. AT1a antagonists or derivatives thereof were suspended in water. Each dose was given via the oral route using a blunt tipped needle by gavage directly into the stomach of each mouse. Dosing was daily in a single administration over a period of seven days.

Figure 15:
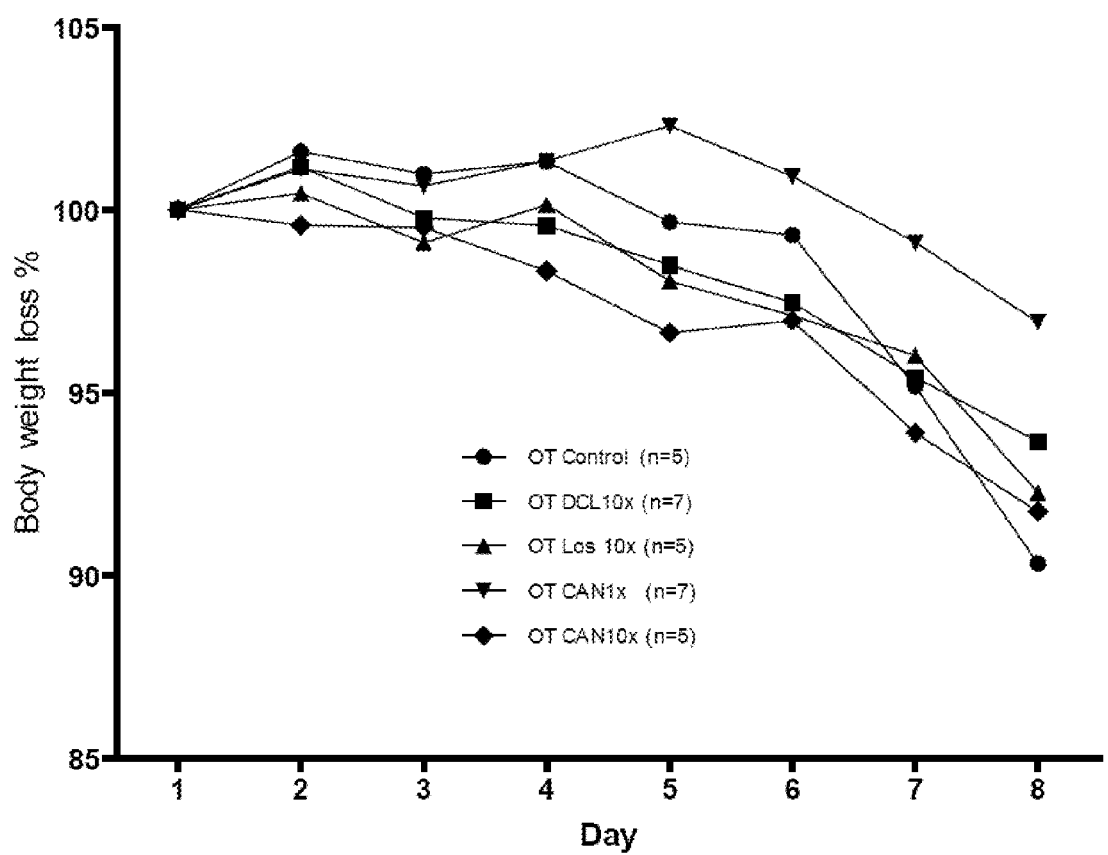
FIG. 15 shows the changes in body weight during seven days of oral administration of AT1a antagonists candesartan (CAN), losarten (Los) and deschlorolosaratan (DCL) in the DSS mouse colitis model.
Figure 16:
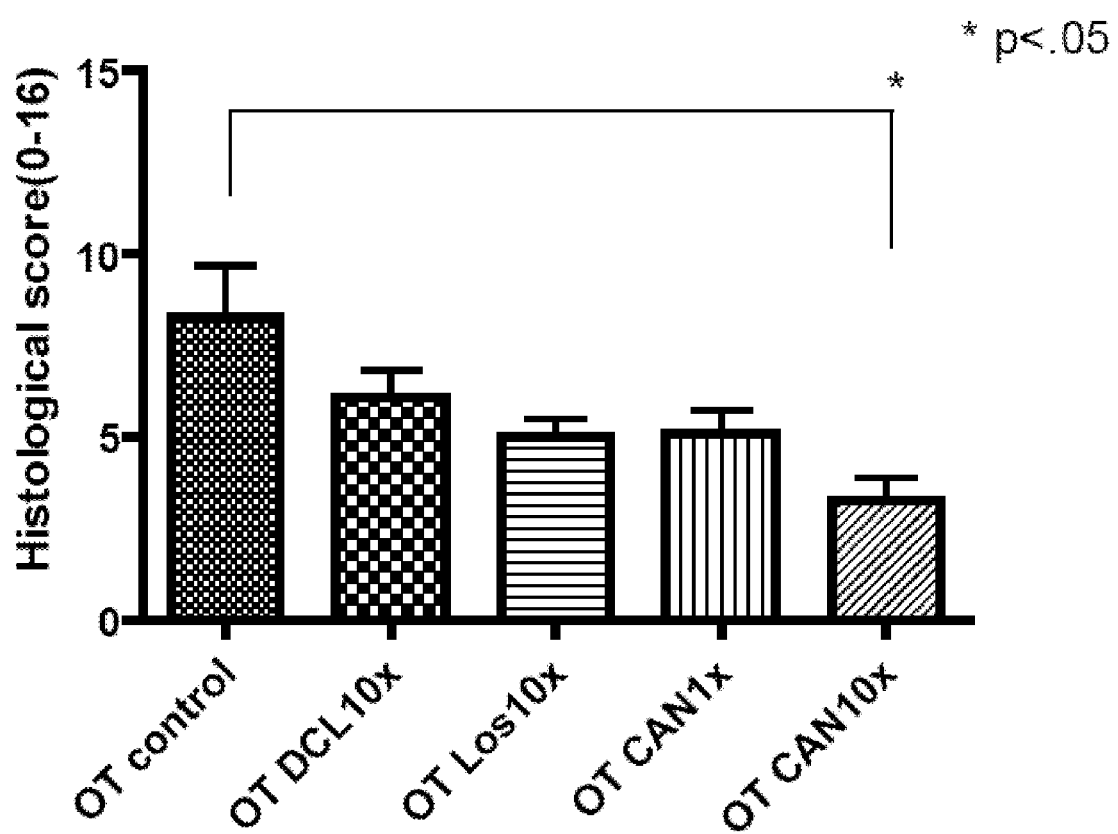
FIG. 16 shows histologic score determined at the completion of seven days of oral administration of AT1a antagonists or derivatives of the same from colonic tissue harvested from the distal ⅓ of the colon in DSS mice.

Changes in Body weight during the seven days of treatment and histologic score determined at the completion of the study from colonic tissue harvested from the distal ⅓ of the colon are shown in FIGS. 15 and 16, respectively. Dosing: AT1a antagonists (candesartan (CAN), losarten (Los) and deschlorolosaratan (DCL)) were given orally (OT, oral therapy) each day. AT1aR antagonists DCL and Los were given at 10-fold (10×) higher doses than typically given systemically (10 mg/kg/day), and candesartan administered at 1 mg/kg/day, and daily dosing was continued for the entire 7 days of the study. Oral treatment (OT) with the AT1a-antagonists prevented weight loss, particularly the use of candesartan (See FIG. 15). Histologic scores were also improved with each AT1a antagonist, particularly with the use of candasartan at the 10× dose (See FIG. 16).

Figure 17:
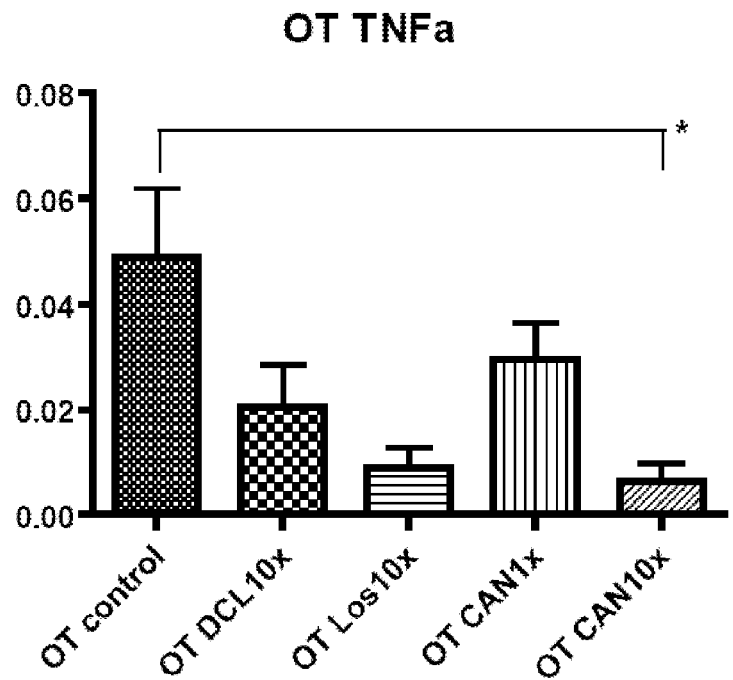
FIG. 17 shows the abundance of mucosal RNA as measured by RT-PCR of several regulatory factors associated with inflammatory bowel disease after oral administration (oral treatment (OT)) with candesartan (CAN), losarten (Los) and deschlorolosaratan (DCL) in the DSS mouse colitis model.
Figure 17:
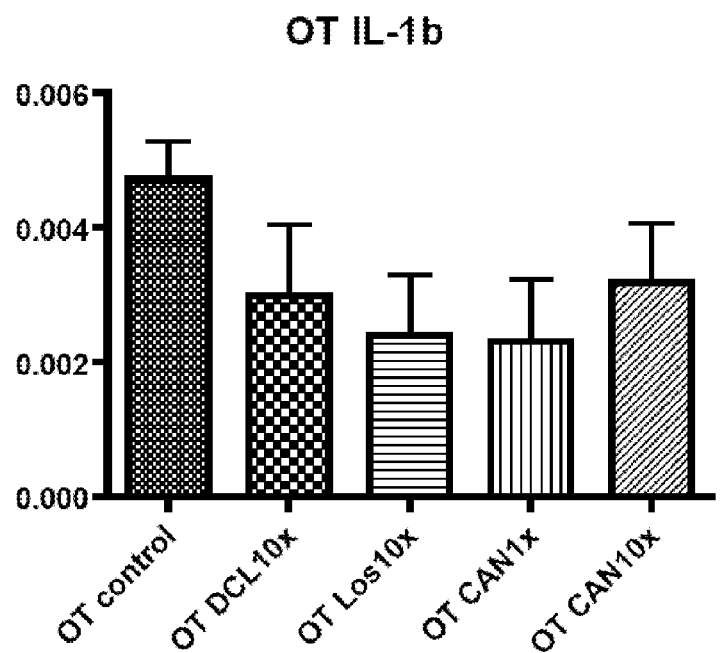
Figure 17:
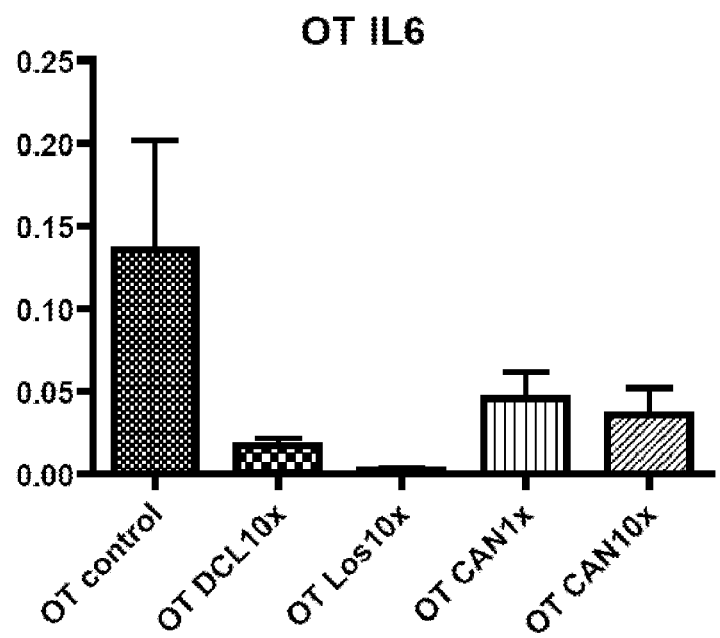
Figure 17:
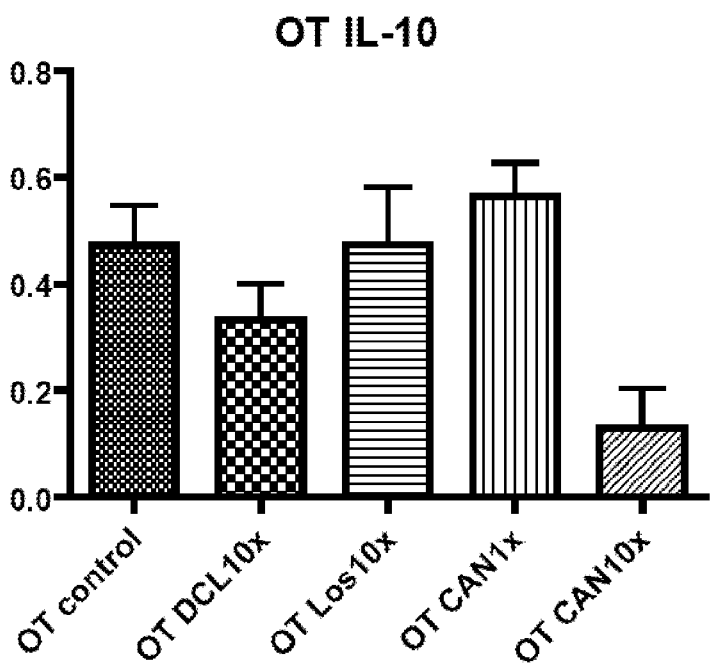
Figure 17:
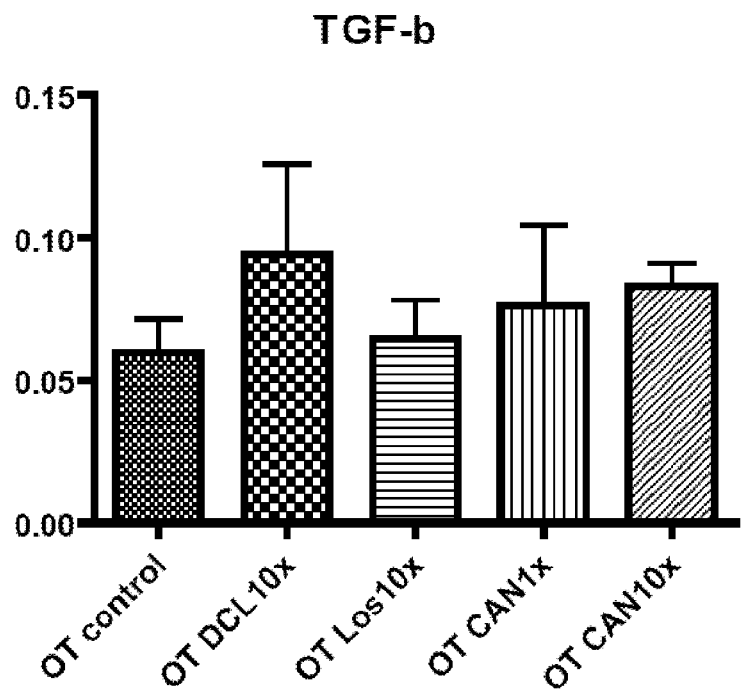
Figure 17:
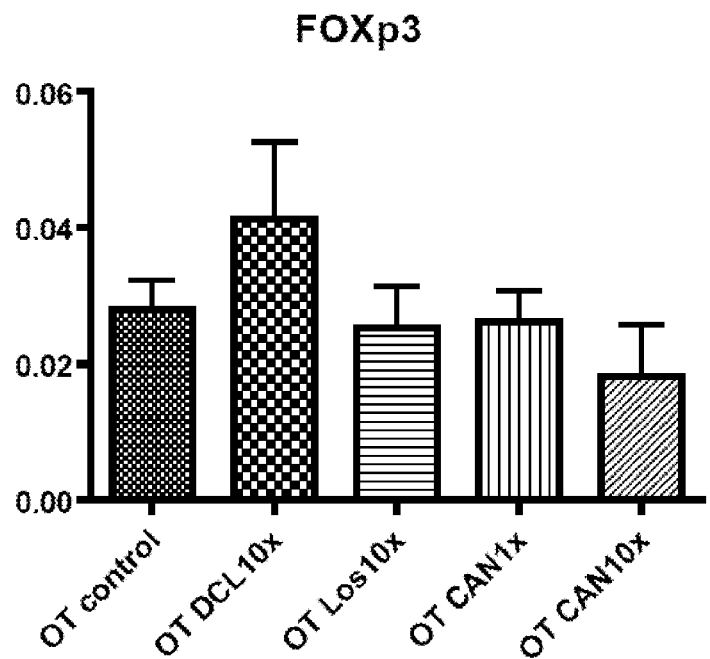

Realtime PCR was utilized to measure the abundance of mucosal RNA of several regulatory factors associated with inflammatory bowel disease. Factors studied were: TNF-α (tumor necrosis factor-alpha); interleukin-1b (IL-1b); IL-6; IL-10; transforming growth factor-beta (TGF-b) and Foxp3 (a T-cell regulatory factor). A marked decline in pro-inflammatory cytokines was observed with oral therapy (See FIGS. 17 A-F).

Figure 18:
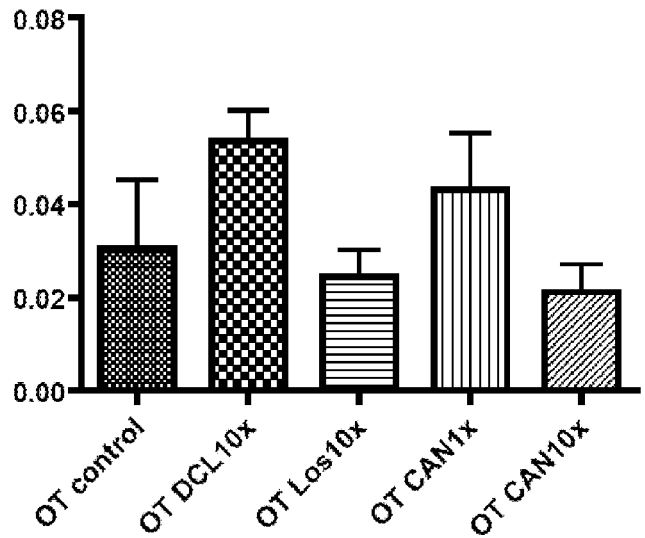
FIG. 18 shows the abundance of mucosal RNA as measured by RT-PCR of several regulatory factors associated with inflammatory bowel disease after oral administration (oral treatment (OT)) with candesartan (CAN), losarten (Los) and deschlorolosaratan (DCL) in the DSS mouse colitis model.
Figure 18:
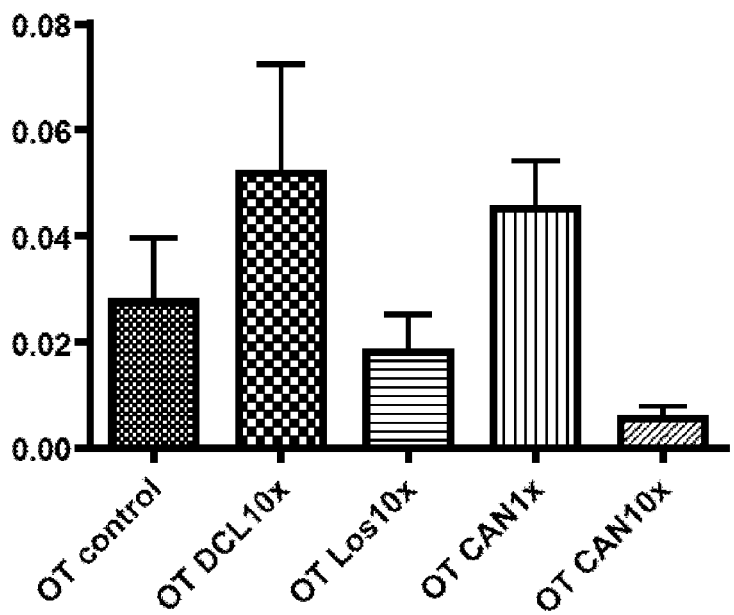
Figure 18:
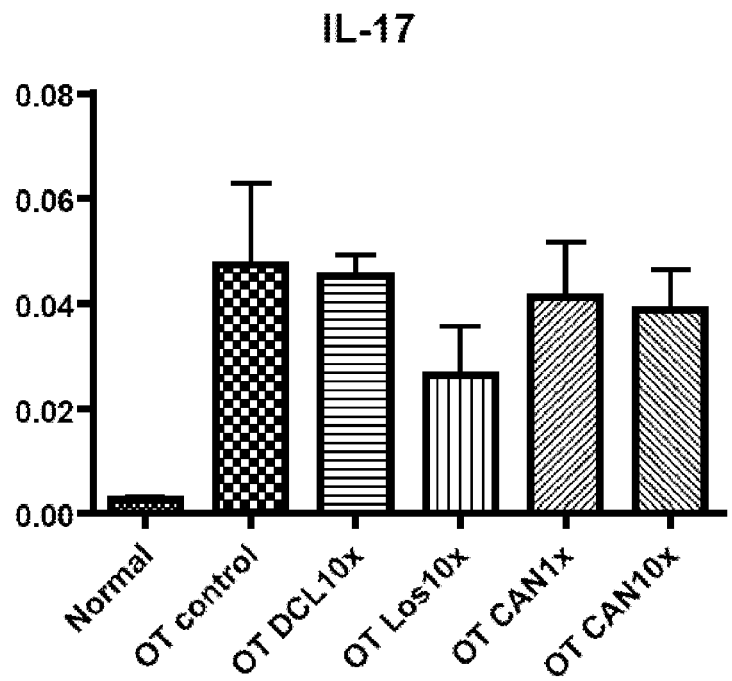
Figure 18:
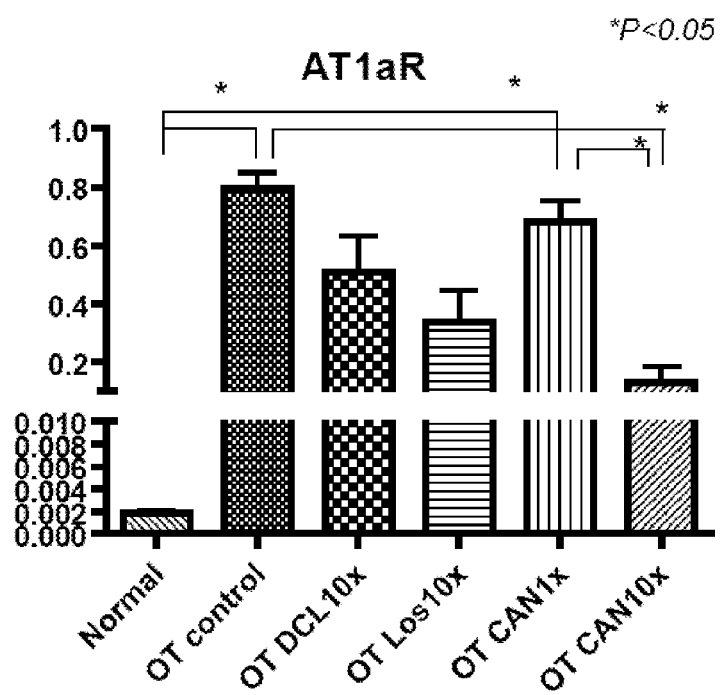
Figure 18:
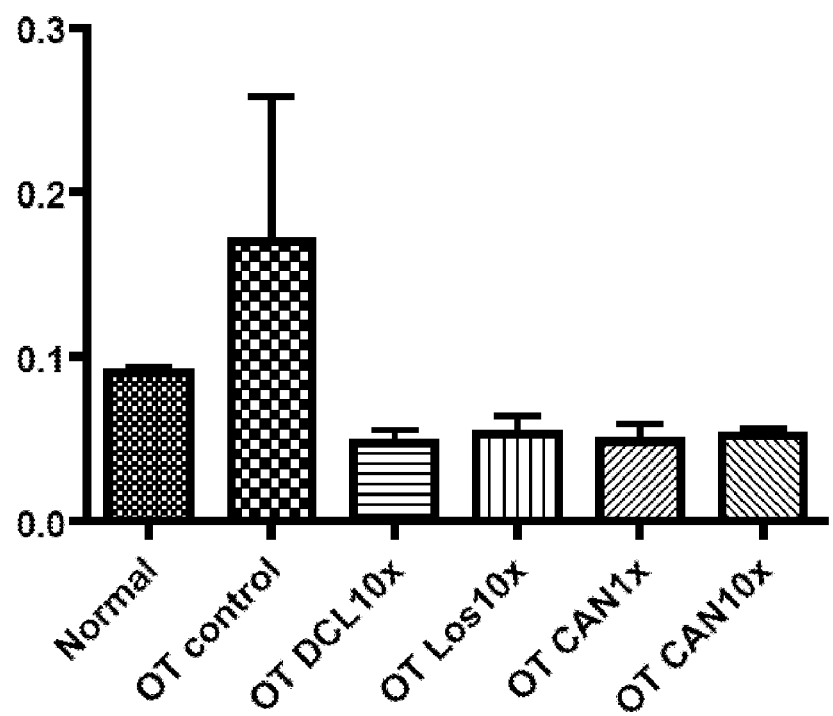

Realtime PCR was also utilized to measure the abundance of mucosal RNA of several additional regulatory factors associated with inflammatory bowel disease. IL-12p40, the regulatory factor for interleukin-12 (IL-12), and a key regulator for the up-regulation of interferon gamma (IFN-g); IFN-g; IL-17, angiotensin II type 1a receptor (AT1aR) and ADAM17 (metallopeptidase domain 17 (ADAM17), also called TACE (tumor necrosis factor-α-converting enzyme). AT1aR antagonists, particularly candesartan (CAN) and losartan (Los) resulted in a marked decline in several of these factors (See FIGS. 18 A-E). Each AT1a antagonist including deschlorolosaratan (DCL) resulted in a marked decline in ADAM17, a factor which is key for activating tumor necrosis factor-alpha.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method of treating a subject, comprising:
 a) providing:
  i) a subject with inflammatory bowel disease, and
  ii) a composition comprising an angiotensin II (AngII) receptor Type 1a (AT1a) antagonist selected from the group consisting of

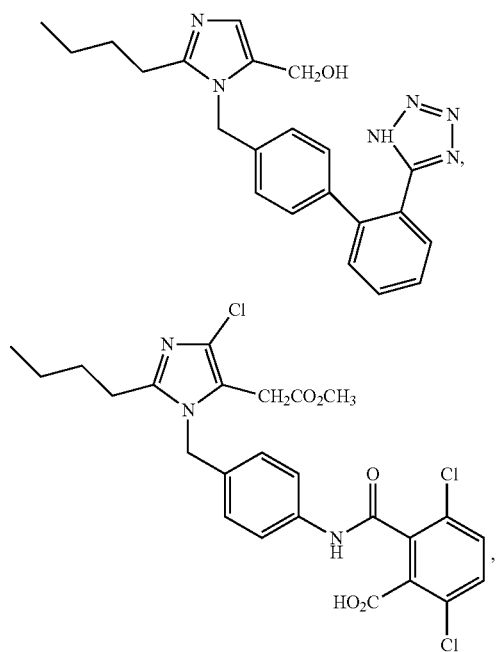

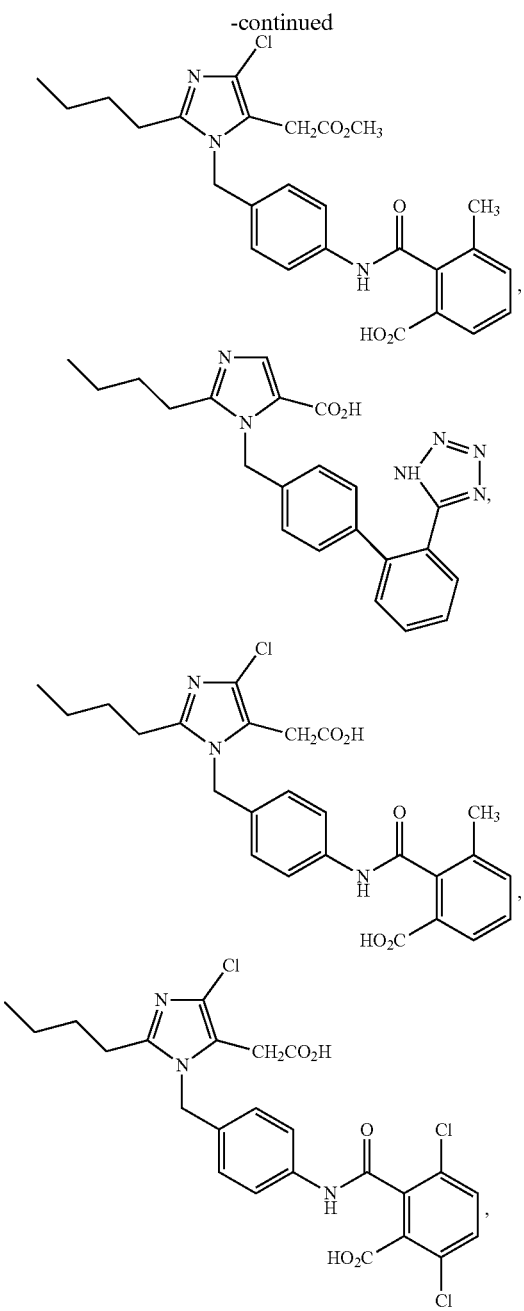

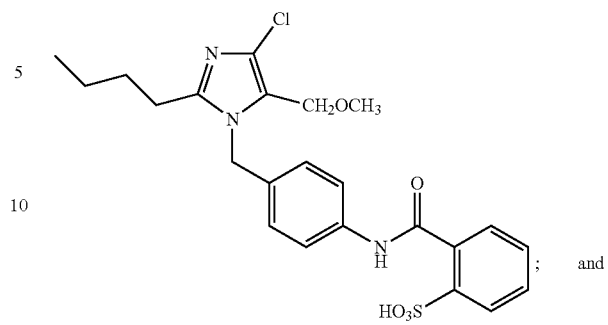

b) administering a therapeutically effective amount of said composition to said subject under conditions such that the severity of inflammatory bowel disease is reduced in said subject.

2. The method of claim 1, wherein said composition comprising an AT1a antagonist is suspended in polyethylene glycol.

3. The method of claim 1, wherein said composition comprising an AT1a antagonist further comprises a corticosteroid.

4. The method of claim 1, wherein said composition comprising an AT1a antagonist is enterally administered.

5. The method of claim 4, wherein administering enterally comprises rectal administration.

6. The method of claim 5, wherein said rectal administration comprises an enema.

7. The method of claim 4, wherein administering enterally comprises oral administration.

8. The method of claim 1, wherein said inflammatory bowel disease is selected from the group consisting of Crohn's disease, celiac disease, ulcerative colitis, diverticulitis, pouchitis, or chronic diarrhea.

9. The method of claim 1, wherein reduction of the severity of inflammatory bowel disease in said subject is detectable by a decrease in the clinical severity of colitis in said subject.

10. The method of claim 1, wherein reduction of the severity of inflammatory bowel disease in said subject is detectable by a reduction in histologic score in said subject.

\* \* \* \* \*